United States Patent
Devaraju et al.

(10) Patent No.: US 10,322,411 B2
(45) Date of Patent: Jun. 18, 2019

(54) SYSTEMS FOR MICROFLUIDIC LOGIC DEVICES

(71) Applicant: Fluidigm Corporation, South San Francisco, CA (US)

(72) Inventors: Naga Gopi Devaraju, San Jose, CA (US); Marc A. Unger, San Mateo, CA (US)

(73) Assignee: Fluidigm Corporation, South San Francisco, CA (US)

( * ) Notice: Subject to any disclaimer, the term of this patent is extended or adjusted under 35 U.S.C. 154(b) by 78 days.

(21) Appl. No.: 15/150,062

(22) Filed: May 9, 2016

(65) Prior Publication Data

US 2016/0250639 A1    Sep. 1, 2016

Related U.S. Application Data

(62) Division of application No. 13/773,518, filed on Feb. 21, 2013, now Pat. No. 9,371,965.

(Continued)

(51) Int. Cl.
*F16K 11/20*    (2006.01)
*B01L 3/00*    (2006.01)
(Continued)

(52) U.S. Cl.
CPC ... *B01L 3/502738* (2013.01); *B01L 3/502707* (2013.01); *B01L 3/502715* (2013.01); *F17D 3/00* (2013.01); *G01N 35/00871* (2013.01); *B01L 2200/14* (2013.01); *B01L 2300/023* (2013.01); *B01L 2300/0816* (2013.01); *B01L 2300/0861* (2013.01); *B01L 2300/0864* (2013.01); *B01L 2300/0867* (2013.01);
(Continued)

(58) Field of Classification Search
CPC ........... B01L 3/502738; F16K 99/0001; F16K 99/0015
See application file for complete search history.

(56) References Cited

U.S. PATENT DOCUMENTS 5,085,562 A    2/1992    van Lintel
5,660,370 A    8/1997    Webster
(Continued)

FOREIGN PATENT DOCUMENTS

WO    2013/126483 A1    8/2013

OTHER PUBLICATIONS

International Search Report and Written Opinion for PCT Application No. PCT/US2013/026985 dated Apr. 23, 2013, 16 pages.
(Continued)

*Primary Examiner* — Reinaldo Sanchez-Medina
(74) *Attorney, Agent, or Firm* — Kilpatrick Townsend & Stockton LLP

(57) ABSTRACT

A microfluidic system includes a substrate, a set of input ports coupled to the substrate, and a set of output ports coupled to the substrate. The microfluidic system also includes a microfluidic processing system coupled to the substrate and including a plurality of processing sites. The microfluidic processing system is coupled to the set of input ports and the set of output ports. The microfluidic system further includes one or more microfluidic logic devices coupled to the substrate and operable to control at least a portion of the microfluidic processing system.

8 Claims, 33 Drawing Sheets

Related U.S. Application Data

(60) Provisional application No. 61/601,456, filed on Feb. 21, 2012.

(51) Int. Cl.
*F17D 3/00* (2006.01)
*G01N 35/00* (2006.01)

(52) U.S. Cl.
CPC ..... *B01L 2300/123* (2013.01); *B01L 2300/14* (2013.01); *B01L 2400/0605* (2013.01); *B01L 2400/0633* (2013.01); *B01L 2400/0655* (2013.01); *G01N 2035/00247* (2013.01); *Y10T 137/7762* (2015.04)

(56) References Cited

U.S. PATENT DOCUMENTS

| | | | |
|---|---|---|---|
| 5,932,799 | A | 8/1999 | Moles |
| 6,619,311 | B2 | 9/2003 | O'Connor et al. |
| 8,220,493 | B2 | 7/2012 | Easley et al. |
| 9,739,295 | B2 * | 8/2017 | Wen .................. F15C 1/003 |
| 2002/0148922 | A1 | 10/2002 | Hayenga et al. |
| 2007/0166199 | A1 * | 7/2007 | Zhou .................. B01L 3/5025 422/400 |
| 2008/0050283 | A1 | 2/2008 | Chou et al. |
| 2009/0217993 | A1 * | 9/2009 | Easley .............. B01L 3/502738 137/565.01 |
| 2010/0233037 | A1 | 9/2010 | Melin et al. |
| 2010/0263757 | A1 | 10/2010 | Fernandes et al. |
| 2011/0301535 | A1 | 12/2011 | Takayama et al. |
| 2012/0128549 | A1 * | 5/2012 | Zhou .................. B01L 3/5025 422/504 |
| 2013/0255799 | A1 | 10/2013 | Devaraju et al. |

OTHER PUBLICATIONS

European Search Report dated Dec. 22, 2015 for EP Patent Application No. 13751323.0, 9 pages.

Frevert et al., "Measurement of cell migration in response to an evolving radial chemokine gradient triggered by a microvalve," Lab on a Chip, 2006, vol. 6. p. 849-856.

Mosadegh, B., "Design and Fabrication of Microfluidic Integrated Circuits using Normally-Closed Elastomeric Valves," Dissertation for Doctor of Philosophy (Biomedical Engineering) in University of Michigan, Jan. 1, 2010, located at http://deepblue.lib.umich.edu/bitstream/handle/2027.42/77762/mosadegh_1.pdf?sequence=1, last visited on Feb. 1, 2016, 178 pages.

Extended European Search Report dated Apr. 8, 2016 for EP Patent Application No. 13751323.0, 14 pages.

Groisman, A. et al. "Microfluidic Memory and Control Devices." *Science*, vol. 300. Published May 2003. 4 pages.

Grover, W. et al. "Development and Multiplexed Control of Latching Pneumatic Valves Using Microfluidic Logical Structures." *Lab on a Chip*, vol. 6, Issue 5. Published May 2006. Retrieved on Aug. 14, 2018. Retrieved from the Internet: URL<http://pubs.rsc.org/en/content/articlehtml/2006/lc/b518362f>. 27 pages.

Hansen, C. et al. "Microfluidics in Structural Biology: Smaller, Faster . . . Better." *Current Opinion in Structural Biology*, vol. 13, Issue 5. Published Oct. 2003. pp. 538-544.

Van Noorst, D. et al. "Fully Controllable Microfluidics for Molecular Computers." *Journal of the Association for Laboratory Automation*, vol. 9, Issue 5. Published Oct. 2004. 6 pages.

Vestad, T. et al. "Flow Resistance for Microfluidic Logic Operations." *Applied Physics Letters*, vol. 84, No. 25. Published Jun. 2004. 2 pages.

Weaver, J. et al. "Static Control Logic for Microfluidic Devices Using Pressure-Gain Valves." *Nature Physics*, vol. 6. Published Mar. 2010. 6 pages.

\* cited by examiner

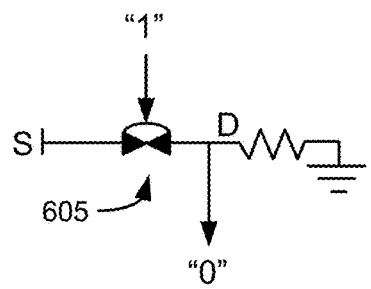
FIG. 6A
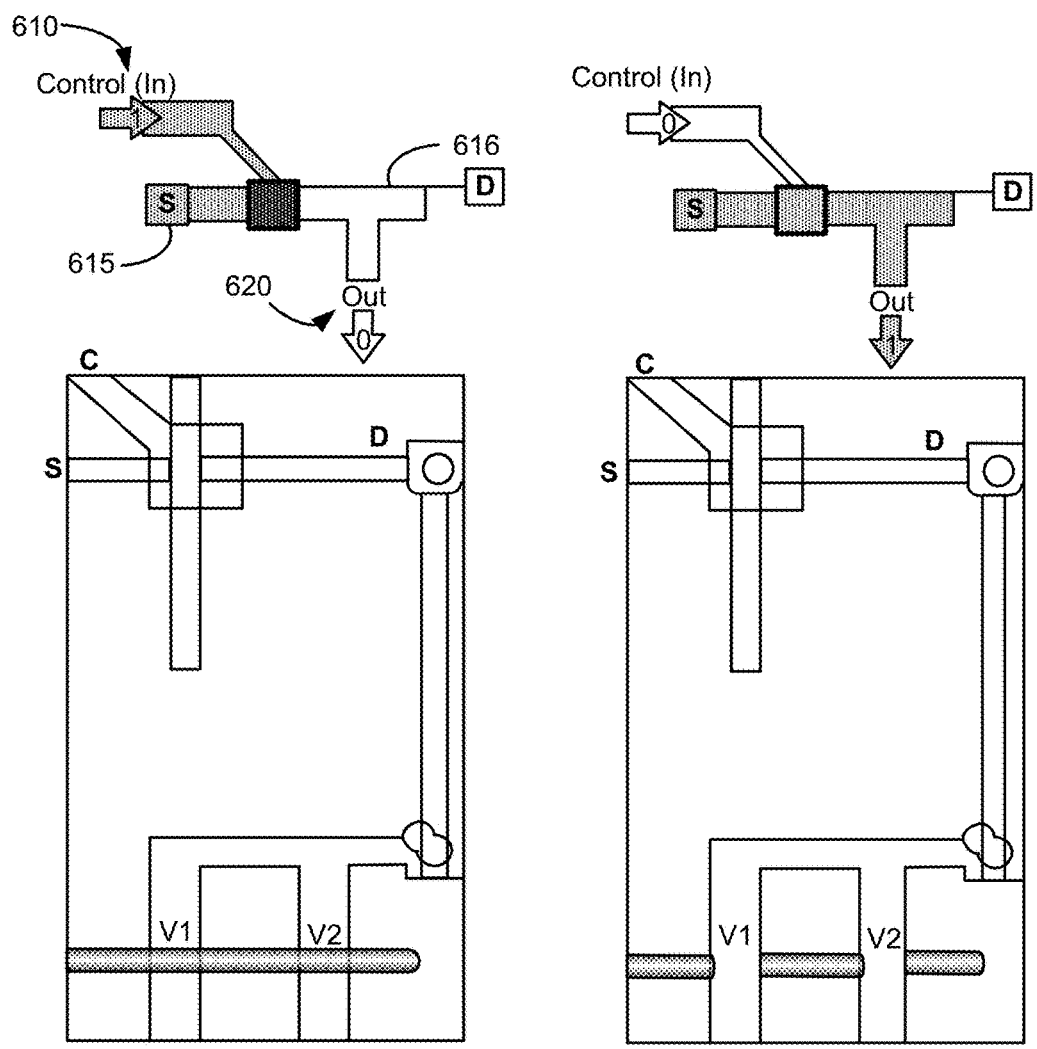
FIG. 6B  FIG. 6C

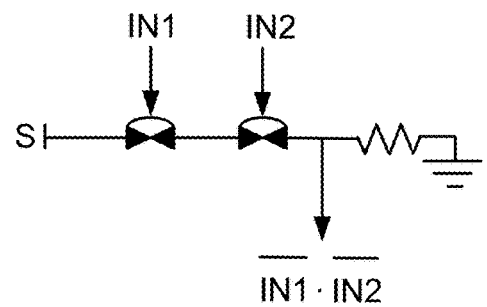
FIG. 7A
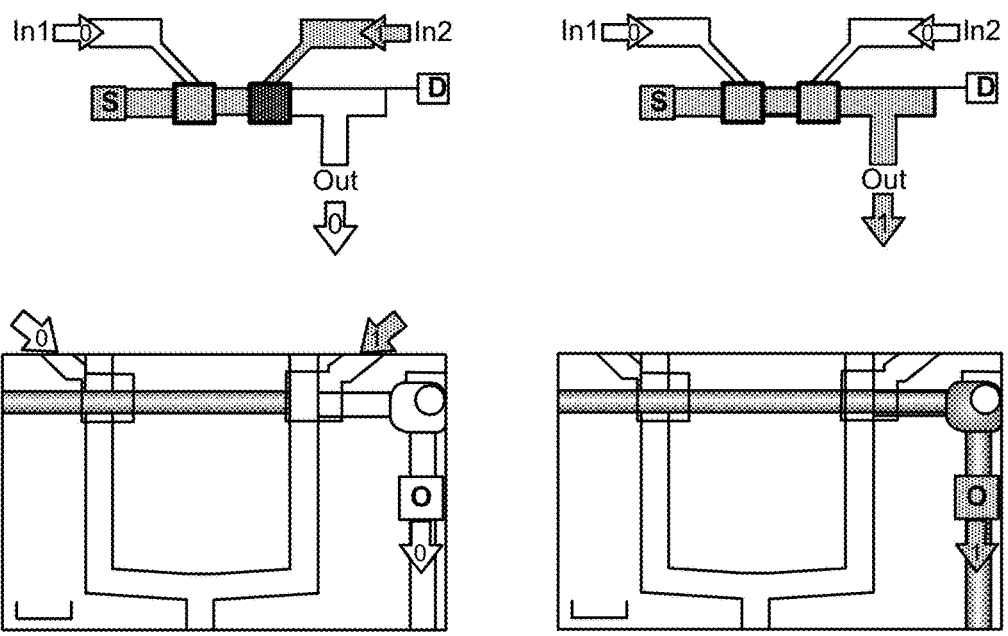
FIG. 7B  FIG. 7C

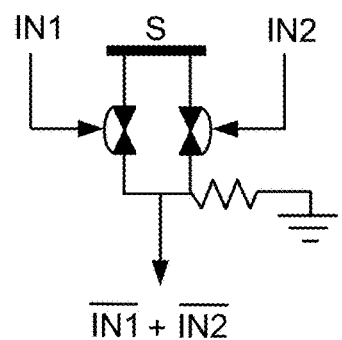
*FIG. 8A*
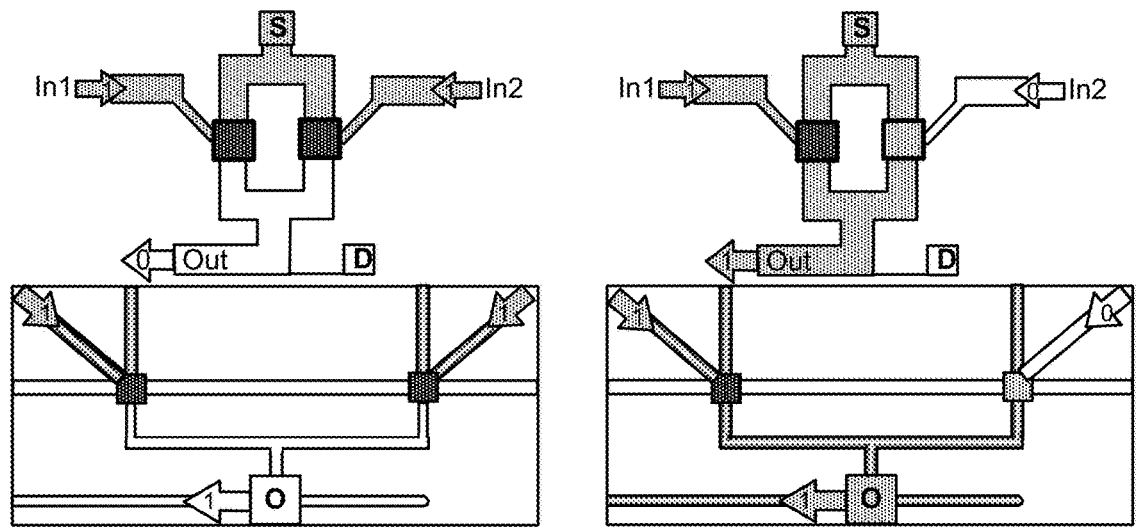
*FIG. 8B*  *FIG. 8C*

FIG. 20A  FIG. 20B

Shift Register

Clock cycle #1

Clock cycle #2

SYSTEMS FOR MICROFLUIDIC LOGIC DEVICES

CROSS-REFERENCES TO RELATED APPLICATIONS

The present application is a divisional of U.S. patent application Ser. No. 13/773,518, filed on Feb. 21, 2013, and entitled "Method and System for Microfluidic Logic Devices," which claims benefit under 35 U.S.C. § 119(e) of U.S. Provisional Patent Application No. 61/601,456, filed on Feb. 21, 2012, and entitled "Method and Systems for Microfluidic Logic Devices," the disclosures of which are hereby incorporated by reference in their entirety for all purposes.

BACKGROUND OF THE INVENTION

Microfluidic technology is revolutionizing biological research and medical diagnostics by reducing analyte and reagent volumes, allowing massive parallelization, and enabling the integration and automation of multiple processes in single devices. Advances in active micro valves using multilayer soft lithography have laid the path to large scale integration of microfluidic components such as valves, pumps, and other active components into full analytical systems. However, the complexity and cost of the control hardware is still a limitation: although a single external control line may be used to control thousands of valves, current microfluidic technologies still require one dedicated external control line for each independently actuated set of valves. This imposes a practical limit on number of independent control operations that can be integrated on to a lab-on-a-chip device and poses a scalability problem.

Microfabricated fluidic chips may be used for biological assays. For example, microfabricated fluidic chips may be used to perform biological assays using external control lines that control the opening and closing of on-chip fluidic valves. The on-chip fluidic valves control the flow of fluids in biological assays. The valves are opened and closed using macroscopic pressure sources that are located off-chip, and which are connected through control lines to the chip. In complex assays, a large number of macroscopic control lines is cumbersome and undesirable. Previously known electrical actuating means built into chips have not been able to provide sufficient force by themselves to open or close fluidic valves in practical situations (e.g., handling liquids at 1-10 psi).

It would therefore be desirable to provide pressure sources and control lines on-chip that control the opening and closing of on-chip valves so that macroscopic control lines exiting the chip are minimized or eliminated. Previously known on-chip systems have not been adequate to provide control of numerous on-chip valves. Therefore, there is a need in the art for improved methods and systems related to microfluidic devices that can provide logic functionality.

SUMMARY OF THE INVENTION

The present invention relates to microfluidic devices. More particularly, the present invention relates to the implementation of fluid logic in microfluidic devices. Merely by way of example, the method and apparatus has been applied to pressure actuated digital logic devices fabricated using multilayer soft lithography in PDMS-based materials. However, it would be recognized that the invention has a much broader range of applicability.

According to an embodiment of the present invention, a microfluidic device is provided. The microfluidic device includes an input source characterized by a source pressure and an input channel in fluid communication with the input source. The microfluidic device also includes an output channel and a valve having an open state and a closed state. The valve is disposed between the input channel and the output channel and is characterized by a static pressure. The microfluidic device further includes a control channel coupled to the valve and characterized by a control pressure. In the closed state, the control pressure is greater than atmospheric pressure.

According to another embodiment of the present invention, a method of fabricating a microfluidic device is provided. The method includes forming a control layer including a control channel and a control layer membrane and forming a flow layer coupled to the control layer. The flow layer includes a flow channel and a flow layer membrane. The method also includes forming a fill layer coupled to the flow layer. The fill layer includes a fill channel and a fill layer membrane. The method further includes injecting a fill material into the fill channel, deflecting a portion of the flow layer membrane to make contact with a portion of the control layer membrane, and curing the fill material.

According to a specific embodiment of the present invention, a microfluidic device is provided. The microfluidic device includes a substrate, a control layer coupled to the substrate, a flow layer coupled to the control layer, and a fill layer coupled to the flow layer. The control layer includes a control channel and a control layer membrane, the flow layer includes a flow channel and a flow layer membrane, and the fill layer includes a fill channel and a fill layer membrane. A portion of the fill layer extends toward the control layer and a portion of the flow layer membrane is in contact with a portion of the control layer membrane.

According to another specific embodiment of the present invention, a microfluidic system is provided. The microfluidic system includes a substrate, a set of input ports coupled to the substrate, and a set of output ports coupled to the substrate. The microfluidic system also includes a microfluidic processing system coupled to the substrate and including a plurality of processing sites. The microfluidic processing system is coupled to the set of input ports and the set of output ports. The microfluidic system further includes one or more microfluidic logic devices coupled to the substrate and operable to control at least a portion of the microfluidic processing system.

According to a particular embodiment of the present invention, a microfluidic device is provided. The microfluidic device includes an input source characterized by a source pressure and an input channel in fluid communication with the input source. The microfluidic device also includes an output channel and a normally closed valve having a closed state and an open state. The normally closed valve is disposed between the input channel and the output channel. The microfluidic device further includes one or more release chambers coupled to a pressure source. Activation of the pressure source deforms the one or more release chambers, placing the normally closed valve in the open state.

According to yet another particular embodiment of the present invention, a control system for a microfluidic device is provided. The control system includes a first microfluidic valve array and a second microfluidic valve array. The control system also includes a first I/O port in fluid communication with a first control line and a second control line and a second I/O port in fluid communication with a third control line and a fourth control line. The control system further includes a first valve having an input coupled to the first control line, an output coupled to the first microfluidic valve array, and a control, a second valve having an input coupled to the second control line, an output, and a control coupled to the third control line, a third valve having an input coupled to the third control line, an output coupled to the second microfluidic valve array, and a control, and a fourth valve having an input coupled to the fourth control line, an output, and a control coupled to the first control line. The control of the first valve is coupled to the output of the fourth valve and the control of the third valve is coupled to the output of the second valve.

Many benefits are achieved by way of the present invention over conventional techniques. For example, embodiments of the present invention provide digital fluidic logic systems analogous to electronic logic. As an example, embodiments of the present invention provide a variant of a normally closed valve exhibiting static gain that is capable of modulating pressure signals in a fashion analogous to an electronic transistor. Using valves described herein, embodiments include complex fluidic logic circuits capable of arbitrary control of fluid flow by processing binary input signals (e.g., HIGH pressure ("1") and LOW pressure, for example, atmosphere, ("0")). Embodiments of the present invention provide fluidic logic that can be implemented in cascaded designs and demonstrates capabilities including feedback, programmability, bi-stability, and autonomous control. Devices with integrated microfluidic control system as provided here reduce external hardware requirements and can be utilized in microfluidic point-of-care and autonomous applications. According to other embodiments, releasable check valves and accumulators are provided that enable control of fluid flow through a microfluidic device. In a specific embodiment, integration of releasable check valves in a microfluidic device reduce system complexity and cost, while increasing device functionality. These and other embodiments of the invention along with many of its advantages and features are described in more detail in conjunction with the text below and attached figures.

BRIEF DESCRIPTION OF THE DRAWINGS

FIG. 6A is a simplified schematic diagram of a NOT gate according to an embodiment of the present invention;

FIG. 6B is an image of a NOT gate with a "1" input according to an embodiment of the present invention;

FIG. 6C is an image of a NOT gate with a "0" input according to an embodiment of the present invention;

FIG. 7A is a simplified schematic diagram of a NOR gate according to an embodiment of the present invention;

FIG. 7B is an image of a NOR gate with a single "1" input according to an embodiment of the present invention;

FIG. 7C is an image of a NOR gate with two "1" inputs according to an embodiment of the present invention;

FIG. 8A is a simplified schematic diagram of a NAND gate according to an embodiment of the present invention;

FIG. 8B is an image of a NAND gate with both inputs set at a high value "1" according to an embodiment of the present invention;

FIG. 8C is an image of a NAND gate with a single "1" input according to an embodiment of the present invention;

FIGS. 20A-20C are simplified schematic diagrams illustrating an oscillator according to an embodiment of the present invention;

DETAILED DESCRIPTION OF SPECIFIC EMBODIMENTS

Figure 1A:
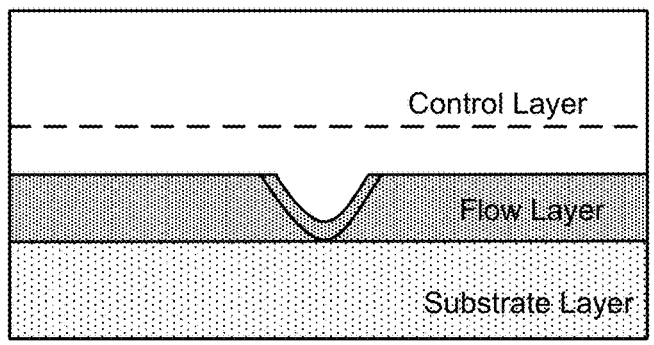
FIG. 1A is a simplified schematic diagram illustrating a normally closed valve (NCV) according to an embodiment of the present invention.

Embodiments of the present invention relate to microfluidic devices. More particularly, the present invention relates to the implementation of fluid logic in microfluidic devices. Merely by way of example, the method and apparatus has been applied to pressure actuated digital logic devices fabricated using multilayer soft lithography in PDMS-based materials. However, it would be recognized that the invention has a much broader range of applicability.

Previously known devices have not been adequate to provide independent control of numerous on-chip valves. Each set of valves typically require a pressure differential between the input and the output to control the valves. Numerous sets of valves coupled together to perform complex functions would therefore require very large number of independent solenoids to drive all of the cascaded valves. Each individual valve structure typically requires a solenoid to turn the pressure ON and OFF. Complex systems that perform numerous functions will therefore require a large, expensive, and complex pressure source that includes many solenoid valves that form pressure I/O connections to the chip from the outside world.

Furthermore, such cascaded valve systems do not allow for the introduction of feedback elements. A feedback element is one whereby a (downstream) output pressure, which is controlled by an upstream valve or is controlled by a valve that is controlled by the upstream valve (and so on), in turn controls the function of the upstream valve. The elimination of the possibility of feedback precludes the construction of entire classes of analog devices and digital logic devices (e.g., latches).

Early forms of fluidic logic were developed as early as the 1960s and largely depended on turbulence effects. This type of fluidic logic however, is not applicable to microfluidics since micro-scale flows are dominated by viscous effects of fluids and the absence of turbulence. Early approaches to implementing logic gates in microfluidics utilized bubbles, relative resistances, electrochemical reaction, or hydrogel. These approaches suffered from having different representations of input and output signals, making them unsuitable for cascading. Some of these are also limited by the types of usable fluids, or by having an output that cannot directly control valves or devices.

As described herein, embodiments of the present invention provide for the integration of fluidic logic control elements at the device level (i.e., on the chip), analogous to logic elements in microelectronics, thereby reducing the number of external chip connections and amount of external control hardware and enabling practical utilization of microfluidics for point-of-care diagnostics and chemical field analysis. To achieve on chip integration, embodiments of the present invention utilize control logic that is capable of both computation (based on input signals and fluidic states in the chip) and control of flow in the chip. Since logical operations are performed by using the output of a gate as an input to the subsequent gate for decision making, the signal is capable of acting on itself for cascade-ability and feedback in circuits. The ability to modulate the signal (gain) is also provided by the implementation of logical operations described herein. In analogy to the transistor, which helped revolutionize the field of electronics by providing a means to modulate the signals allowing electronic signals to operate on each other, microfluidics utilize a fluidic equivalent capable of allowing fluidic signals to operate on each other. State based, pressure driven logic circuits are utilized herein and create fast operating fluidic circuits capable of independent control of multiple devices simultaneously.

Although advances in microfluidics now allow an unprecedented level of parallelization and integration of biochemical reactions, a challenge has been the complexity and cost of the control hardware: one external pressure signal has typically been required for each set of independently actuated valves on a chip. Embodiments of the present invention address this challenge by providing a form of digital fluidic logic fully analogous to electronic logic. Using a Multilayer Soft Lithography (MSL) fabrication process, embodiments provide a normally closed static gain valve capable of modulating pressure signals in a fashion analogous to an electronic transistor. These valves are then used in implementing complex fluidic logic circuits capable of arbitrary control of flows by processing binary input signals (pressure (1) and atmosphere (0)). As examples, logic gates and devices including NOT, NAND and NOR gates, bi-stable flip-flops, gated flip-flops (latches), oscillators, self-driven peristaltic pumps, and delay flip-flops are provided using static gain valves fabricated according to embodiments of the present invention. In a particular implementation, a fluidic microprocessor analogous to a serial-in parallel-out shift register capable of processing 12 bits of information is operated at clock rates as high as 10 Hz. The fluidic logic devices described herein provide cascade-ability, feedback, programmability, bi-stability, and/or autonomous control capabilities. Devices with integrated microfluidic control systems provided according to embodiments of the present invention help reduce the external hardware requirements and may lead to broader application of microfluidics in point-of-care and autonomous applications.

Figure 1B:
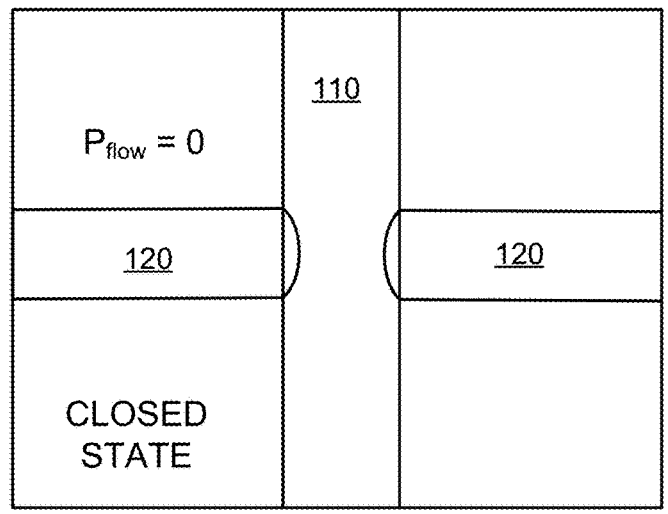
FIG. 1B is an image of the NCV in a closed state.
Figure 1C:
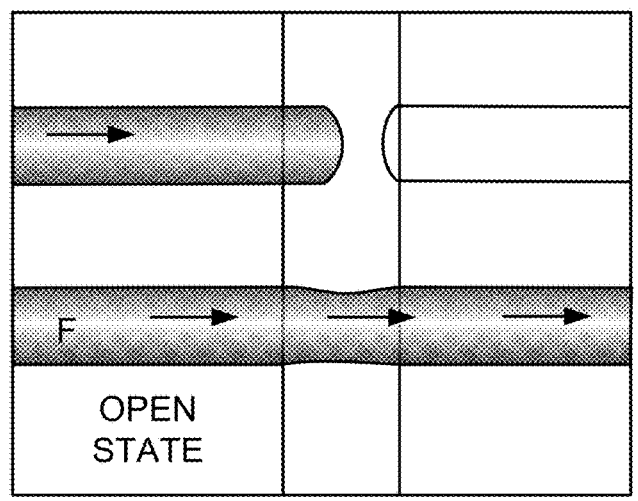
FIG. 1C is an image of the NCV entering into an open state and in the open state.

Embodiments of the present invention integrate fluidic logic functionality on PDMS chips without adding complexity to the fabrication process. FIG. 1A is a simplified schematic diagram illustrating a normally closed valve (NCV) according to an embodiment of the present invention. The NCV includes several layers, including a substrate layer (also referred to as a blank layer), a flow layer, and a fill/control layer as illustrated in FIG. 1A. FIG. 1B is an image of the NCV in a closed state and FIG. 1C is an image of the NCV entering into an open state and in the open state. The NCV is characterized by a breakthrough pressure (BP)—the minimum pressure required in the flow channel to open the NCV and to enable fluid to pass through the valve. That is, once the flow pressure in the flow channel is greater than the breakthrough pressure, the valve opens, allowing fluid to flow through the flow channel.

Referring to FIG. 1B, the NCV in the illustrated embodiment is formed at the intersection of the control channel 110 (vertical channel) and the flow channel 120 (horizontal channel), which are separated by a flexible membrane. As described more fully below, the NCV fabrication process includes filling the control channel (i.e., the vertical channel in FIG. 1B) with a material that sets in the channel (e.g., a flash curable material that is cured under pressure when the valve is in the closed condition). The material in the control channel (e.g., a cured structure) exerts a force on the membrane (i.e., the valve membrane) to keep the valve closed in the normally closed state. As illustrated in FIG. 1C, as the pressure in the flow channel 120 increases as a result of an increase in the pressure in the flow channel ($P_{flow}$), the valve begins to open as illustrated in the upper portion of the figure and then fully opens, passing fluid through the valve, as the pressure in the flow channel exceeds the breakthrough pressure ($P_{flow} \geq BP$).

Figure 2A:
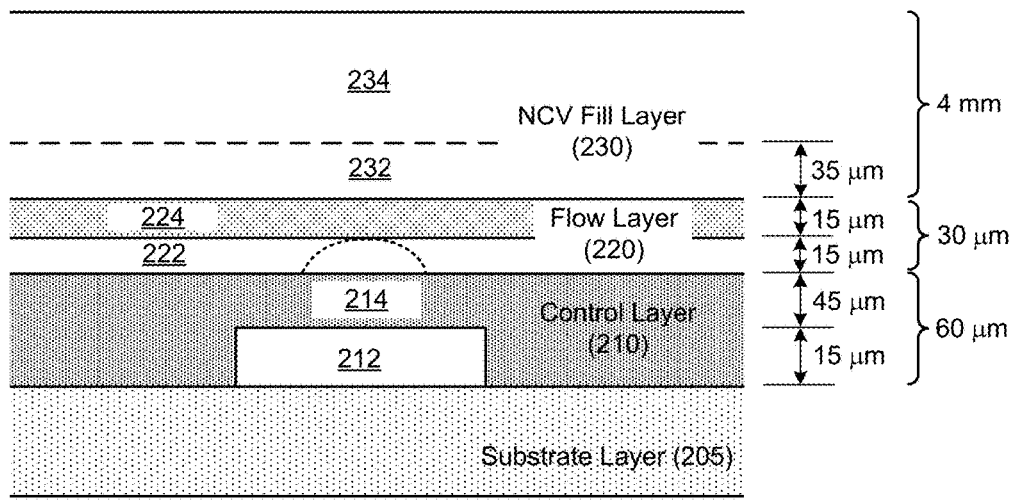
FIG. 2A is a simplified schematic diagram illustrating an NCV during a first stage of fabrication according to an embodiment of the present invention.

FIG. 2A is a simplified schematic diagram illustrating a static gain valve 200 during a first stage of fabrication according to an embodiment of the present invention. As illustrated in FIG. 2A, a substrate layer 205 (also referred to as a blank layer) is used as a support layer for the other layers fabricated in the microfluidic structure. In some embodiments, the substrate layer 205 is a material with mechanical rigidity and chemical stability, such as PDMS, glass, plastic, elastomeric materials, a silicon substrate, combinations thereof, or the like.

The static gain valve 200 also includes a control layer 210 including a control channel 212 and a control membrane 214. In some embodiments, the control channel supports a fluid pressure (e.g., a pressurized gas) that is able to deflect the control membrane 214 into the flow channel of the flow layer, providing control over the operation of the valve. The material and thicknesses for the elements of the control layer 210 can vary depending on the particular application. As an example, the control channel 212 can have a height ranging from about 10 µm to about 100 µm, for example 15 µm and width ranging from about 10 µm to about 200 µm, for example 100 µm. The thickness of the control membrane 214 can vary, depending on the particular application. As an example, the control membrane can have a height (thickness) ranging from about 10 µm to about 100 µm, for example 45 µm and width ranging from about 50 µm to about 500 µm, for example 300 µm. The materials used to fabricate the control layer can include elastomeric polymers such as PDMS, polyurethanes, acrylic polymers, combinations thereof, or the like. Additional description related to elastomeric polymers suitable for use in devices described herein is provided below.

Elastomers in general are polymers existing at a temperature between their glass transition temperature and liquefaction temperature. See Allcock et al., Contemporary Polymer Chemistry, 2nd Ed. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa-1 TPa, more preferably between about 10 Pa-100 GPa, more preferably between about 20 Pa-1 GPa, more preferably between about 50 Pa-10 MPa, and more preferably between about 100 Pa-1 MPa are useful in accordance with the present invention, although elastomeric materials having a Young's modulus outside of these ranges could also be utilized depending upon the needs of a particular application.

Given the tremendous diversity of polymer chemistries, precursors, synthetic methods, reaction conditions, and potential additives, there are a huge number of possible elastomer systems that could be used to make the devices of the invention. Common elastomeric polymers include perfluoropolyethers, polyisoprene, polybutadiene, polychloroprene, polyisobutylene, poly(styrene-butadiene-styrene), polyurethanes, and silicones, for example, or poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon), polydimethylsiloxane, polydimethylsiloxane copolymer, and aliphatic urethane diacrylate. For illustration, a brief description of the most common classes of elastomers is presented here:

Silicones: Silicone polymers have great structural variety, and a large number of commercially available formulations. In an exemplary aspect of the present invention, the present systems are fabricated from an elastomeric polymer such as GE RTV 615 (formulation), a vinyl-silane crosslinked (type) silicone elastomer (family). The vinyl-to-(Si—H) crosslinking of RTV 615 allows both heterogeneous multilayer soft lithography and photoresist encapsulation. However, this is only one of several crosslinking methods used in silicone polymer chemistry and suitable for use in the present invention. In one embodiment, the silicone polymer is polydimethylsiloxane (PDMS).

Perfluoropolyethers: Functionalized photocurable perfluoropolyether (PFPE) is particularly useful as a material for fabricating solvent-resistant microfluidic devices for use with certain organic solvents. These PFPEs have material properties and fabrication capabilities similar to PDMS but with compatibility with a broader range of solvents. See, e.g., PCT Patent Publications WO 2005030822 and WO 2005084191 and Rolland et al., 2004, "Solvent-resistant photocurable "liquid Teflon" for microfluidic device fabrication" J. Amer. Chem. Soc. 126:2322-2323.

Polyisoprene, polybutadiene, polychloroprene: Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). Homogeneous multilayer soft lithography would involve incomplete vulcanization of the layers to be bonded and photoresist encapsulation would be possible by a similar mechanism.

Polyisobutylene: Pure Polyisobutylene has no double bonds, but is crosslinked to use as an elastomer by including a small amount (.about.1%) of isoprene in the polymerization. The isoprene monomers give pendant double bonds on the polyisobutylene backbone, which may then be vulcanized as above.

Poly(styrene-butadiene-styrene): Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes: Polyurethanes are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

The selection of materials (whether elastomeric or non-elastomeric) will take into account the need for particular material properties and will depend on a variety of factors including: ease of manufacture, the nature of the chemical synthesis, solvent resistance and temperature stability. For example, fluidic circuits fabricated from PDMS will not be compatible with all organic solvents (see, e.g., Lee et al., 2003, Anal. Chem. 75:6544-54). This issue can be addressed by the use of chemically resistant elastomers in place of PDMS in at least some regions of the device. For example, perfluoropolyether (PFPE) can be used (see Rolland et al., 2004, "Solvent-resistant photocurable "liquid Teflon" for microfluidic device fabrication" J. Amer. Chem. Soc. 126: 2322-23, and citations herein above). Alternatively, the elastomer (e.g., PDMS) surface can be chemically modified to increase compatibility with organic solvents and improve function Methods and reagents for such modification include those described in US 2004/0115838 [para. 0293] et seq.; copolymers of tetrafluoroethylene, perfluoromethylvinylether (also called TFE-perfluorovinylether polymers) such as Chemraz (Greene-Tweed, 10% solution) diluted 1:1 in low boiling point perfluorocarbon liquid, e.g. Flourinert from 3M), Kalrez (Du Pont), Chemtex (Utex Industries), and fluorocarbon polymers (FKM, e.g. poly(tetrafluoro-co-hexafluoropropylene) such as Cytop coating (poly(perfluoro (alkenyl vinyl ether) from Bellex International Corp. and Novec EGC-1700 coating (fluoroaliphatic polymer) from 3M which can be applied by flushing the solutions though channels (e.g., 3.times.40 microliters at 25 psi, at 1 min intervals). In addition, many chemical reactions can be carried out in a variety of solvents. Reaction series to be carried out in a chip made using particular materials can be designed to use solvents that are compatible with the materials over the period of time necessary to complete the reaction.

For devices made using multilayer soft lithography (in which layers of elastomer are cured separately and then bonded together) another important consideration for fabrication is the ability to bond multiple layers of elastomers together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers, the use of thermoset elastomers, and use of composite structures.

Referring to FIG. 2A, the flow layer 220 includes a flow channel 222 and a flow layer membrane 224. As illustrated in FIG. 2A, the orientation of the flow channel 222 (lying in the plane of the figure) is orthogonal to the orientation of the control channel 212 (extending into the plane of the figure), although this is not required by embodiments of the present invention. In some embodiments as illustrated below, the control channel can be formed as a chamber underlying the flow channel to form the valve, with lateral dimensions greater than the lateral dimensions of the flow channel. The material and thicknesses for the elements of the flow layer 220 can vary depending on the particular application. As an example, the flow channel 222 can have a height ranging from about 1 µm to about 100 µm, for example 15 µm and width ranging from about 10 µm to about 200 µm, for example 100 µm. The thickness of the flow layer membrane 224 can vary, depending on the particular application. As an example, the flow layer membrane can have a height (thickness) ranging from about 5 µm to about 50 µm, for example 15 µm and width ranging from about 20 µm to about 200 µm, for example 100 µm. The materials used to fabricate the flow layer can include elastomeric polymers such as PDMS, polyurethanes, acrylic polymers, a Si wafer, combinations thereof, or the like.

An NCV fill layer 230 is also provided adjacent the flow layer 220 and is used to transfer a portion of the material used during the construction of the static gain valve. Initially, a fill channel 232 (that is able to receive and transfer a flow of fill material) of the fill layer 230 is free of material, providing for a flow of material into the structure to deflect the flow layer membrane 224 and form the valve portion of the static gain valve. As illustrated in FIG. 2A, the thickness of the fill channel 232 is 35 µm, although other thicknesses can be utilized, for example, thicknesses ranging from about 5 µm to about 300 µm.

Figure 2B:
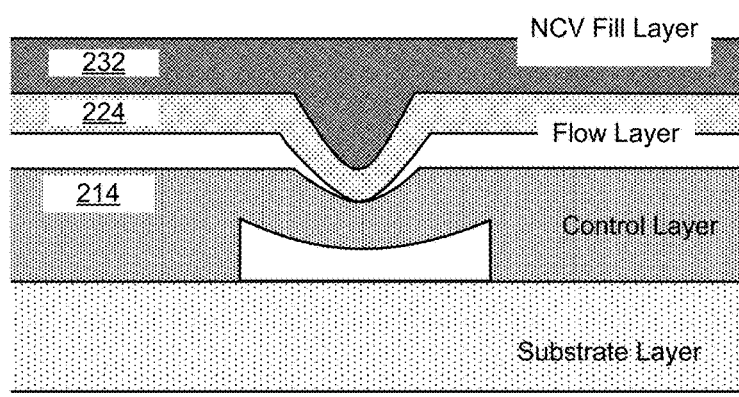
FIG. 2B is a simplified schematic diagram illustrating the NCV of FIG. 2A during a second stage of fabrication according to an embodiment of the present invention.

The NCV fill layer can also be referred to as Source layer. Although the cross section illustrated in FIG. 2B illustrates the NCV fill layer as being filled with the cured fill material, thereby exerting pressure to form the normally closed valve, this layer also includes a channel network (for example, 100 µm-300 µm wide) (not shown) that has a number of large chambers/channels that serve as large reservoirs for the pressure source and the drain for the chip by delivering the desired pressure to all the source ports and connecting the drain ports to atmosphere. Thus, all logic elements can be coupled to one or more common input reservoirs. The NCV fill layer 230 also contains the network of channels to fabricate the normally closed valves. The external connections, including pressure and atmospheric connections, are made through punches (~700 um in size in some examples)

in this layer. The flow channels in the flow layer can be rounded in cross section in some embodiments. The flow layer includes elements of the NCVs and acts as the signal transfer layer, thereby providing most of the logic circuitry. The source port connections to the reservoir in the source layer, as well as other layer-to-layer connections for signal transport were made using ~60 µm punches. The control channels receive the input signal from flow/signal transport layer and deliver the signals to the membranes for the valve control. Although not shown in FIG. 2B, an additional sealing layer is provided in some embodiments as a thick blank sealing layer for the channels in the control layer (e.g., 4 mm thick) that also serves to provide substrate functionality.

FIG. 2B is a simplified schematic diagram illustrating the static gain valve 200 during a second stage of fabrication according to an embodiment of the present invention. As illustrated in FIG. 2B, the fill channel 232 of the fill layer 230 has been filled with a material that fills the fill channel 232 and deflects the flow layer membrane 224 toward the control layer, making contact between the lower surface of the flow layer membrane 224 and the lower surface of the flow channel 222 (i.e., the upper surface of control membrane 214), thereby closing the valve as a result of the flow layer membrane being pinned against the control membrane surface. Once the material has filled the fill channel 232, a curing process is utilized under pressure to set the material in the cured state as illustrated in FIG. 2B. The break through pressure associated with the device will be a function of the process used to fill the fill channel and the pressure associated with the contact between the flow layer membrane and the control layer membrane. The static pressure of the valve can be increased by increasing the break through pressure using a higher fill line pressure during the fabrication of the static gain valve, resulting in an increased pressure with which the flow layer membrane is deflected towards and making contact with the control membrane.

In an embodiment, the normally closed valve (NCV) is fabricated by pressurizing the NCV fill channel(s) with a UV flash-curable material and curing under pressure (i.e., a fill line pressure equal to $P_{FL}$) so that the valve is in closed condition. The material cures into a hard structure forming an NCV in the flow channel disrupting its continuity. The break through pressure of the NCVs can be tuned in both the design stage and the fabrication stage. The break through pressure depends in some embodiments on two factors: the fill line pressure of the NCV and the valve geometry. NCVs are characterized by the threshold pressure to open the valve, which is the pressure used to generate the force required to open the blocking structure of the NCV, which has been referred to as the break through pressure (BP). The pressure at which the fill material is filled and cured in the NCV fill layer is referred to as fill line pressure ($P_{FL}$) and determines the built-in pressure of the normally closed valve.

In an exemplary embodiment, the NCV fill channels crossing the bottom flow channel were filled with a curable material that was subsequently cured with the valve in closed condition under pressure. As an example, a low viscosity UV curable reactive acrylate monomer (ditrimethylolpropane tetraacrylate, SR355, Sartomer) mixed with 10% initiator (Esacure KT-046) was used as the UV curable filler material to fabricate NCVs. Curing was performed by exposing the material to 365 nm UV light (~275 MW/cm$^2$) for 2.5 minutes. A variety of curable materials can be utilized according to embodiments of the present invention, including Acrylates, Urethanes, siloxanes, epoxies, and the like as well as soft and hard elastomers and plastics.

In addition to light-based (e.g., UV, visible, and the like) curing, other curing processes, including thermal curing, including free radical, ionic polymerization, and the like, can be utilized. In some process flow, the NCV fabrication is performed at a predetermined time (e.g., at least a day) after the fabrication of the underlying to reduce or eliminate any undesired permanent bonding at the NCV resulting from residual surface activation during the chip fabrication. The cured NCV structure forces the flow layer membrane down as shown in FIG. 2B and exerts a pressure disrupting the continuity of the flow channel.

As an example of a fabrication process, the channels and layers illustrated in FIGS. 2A and 2B, used patterned molds that were prepared on 6" Si wafers. SU-8 negative photoresist was used for the NCV fill layer and the control layer and SPR220 positive photoresist was used in forming flow layer molds. The channel heights (i.e., equal to the photoresist thickness) were controlled by rate of spin coating. Photoresist was then exposed to 365 nm UV light through masks and subsequent baking and developing of the photoresist resulted in the formation of the patterned molds. These molds were then used to fabricate layers with features in PDMS.

In a particular embodiment, layers were fabricated from PDMS (RTV-615). The mix ratio for the prepolymer to crosslinker used was 10:1 for the layers. Parts A and B were mixed in a vacuum mixer for 120 seconds at 1200 rpm to avoid air entrapment. Molds were surface treated with TMCS to keep PDMS from sticking to the mold surfaces.

The NCV fill layer was fabricated by injecting RTV-615 into the mold and curing at 100° C. for 1 hour in a convection oven to produce a patterned layer about 4 mm thick. The cured layer was peeled from the mold and manually punched for external connections. Flow layer and control layer molds were spin coated with RTV-615 (~30 µm thick and ~45 µm thick, respectively) and then cured and bonded at 100° C. for 1 hour. Fluid connections between layers were formed using vias between layers ~60 µm in diameter.

It should be noted that since the static pressure gain is dependent on the breakthrough pressure of the normally closed valve, it is possible to tune the static gain to a predetermined value by controlling the break through pressure of the valve. The breakthrough pressure of a NCV can be tuned during design and fabrication of the device and primarily depends on two parameters—(1) fill line pressure of the normally closed valve and (2) geometry of the valve. A higher fill pressure results in a larger NCV structure, which then exerts more force on the valve and leads to a higher break through pressure. Change in the break through pressure as a function of the fill line pressure was determined by the inventors. The geometry of the valve from which the NCV is fabricated also influences the break through pressure. Building normally closed valves from bigger valves and thinner membranes results in an increase in break through pressure for at least two reasons: (1) effective fill line pressure of the valves increases since the membranes deflect at lower pressures, and (2) the resulting valve structure is bigger, stronger, and exerts a higher force. Although the break through pressure of the normally closed valve can be increased by increasing the size of the valve, the inventors have determined that starting from a valve that has wider fill channel and keeping the same flow channel cross section is an effective method to increase the break through pressure. Without limiting embodiments of the present invention, the inventors believe that this result is because narrower flow channels require a higher flow pressure to generate the same force as compared to a wider flow channel.

Figure 2C:
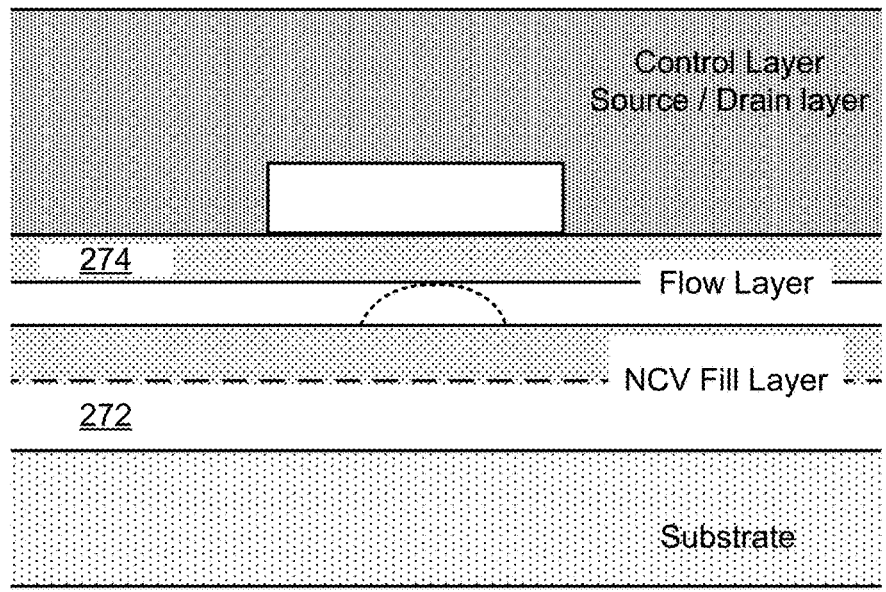
FIG. 2C is a simplified schematic diagram illustrating an NCV during a first stage of fabrication according to an alternative embodiment of the present invention.

FIG. 2C is a simplified schematic diagram illustrating an NCV during a first stage of fabrication according to an alternative embodiment of the present invention. As illustrated in FIG. 2C, the gain valve geometry has been modified such that the NCV fill layer including the fill channel 272 is positioned below the flow layer including the flow layer membrane 274.

Figure 2D:
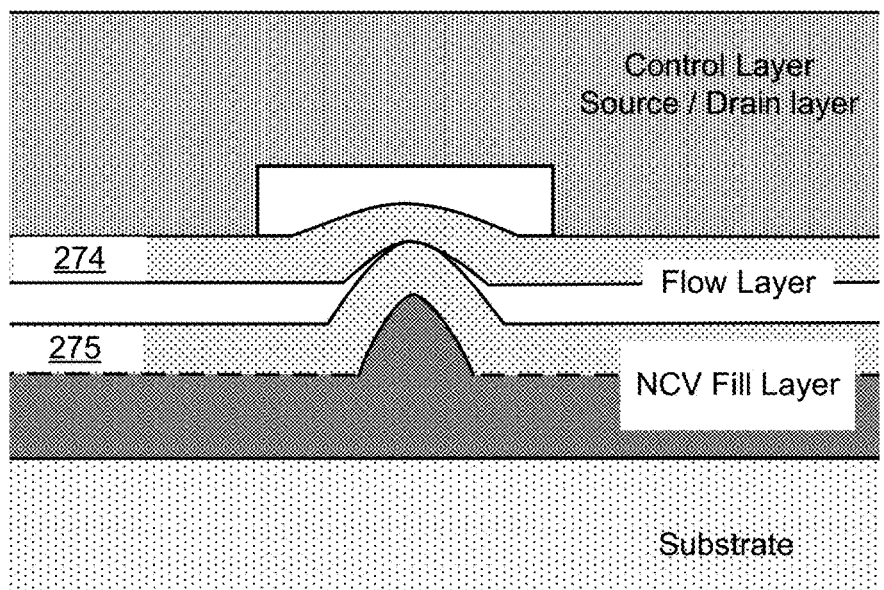
FIG. 2D is a simplified schematic diagram illustrating the NCV of FIG. 2C during a second stage of fabrication according to an alternative embodiment of the present invention.

FIG. 2D is a simplified schematic diagram illustrating the NCV 270 of FIG. 2C during a second stage of fabrication according to an alternative embodiment of the present invention. As illustrated in FIG. 2D, in implementations in which the NCV fill layer is positioned below the flow layer, the fill layer membrane 275 deflects the flow layer membrane 274 into the control layer such that the flow layer membrane 274 contacts the lower surface of the control layer. Also in this implementation, the control layer will act as the source/drain layer because the top layer can be fabricated with a thickness greater than the other layers and, thereby, provide a suitable in which reservoirs/large chambers can be incorporated.

Thus, embodiments of the present invention are not limited to a geometry in which the control layer is bonded to the substrate layer. Rather, embodiments in which the NCV fill layer is positioned below the flow layer and the control layer are provided as illustrated in FIGS. 2C and 2D. In yet other alternative embodiments, the static gain valve can be fabricated such without the control layer being adjacent to the flow layer. In the embodiments, the flow layer can be bonded to the substrate, providing another alternative geometry. One of ordinary skill in the art would recognize many variations, modifications, and alternatives.

Figure 3A:
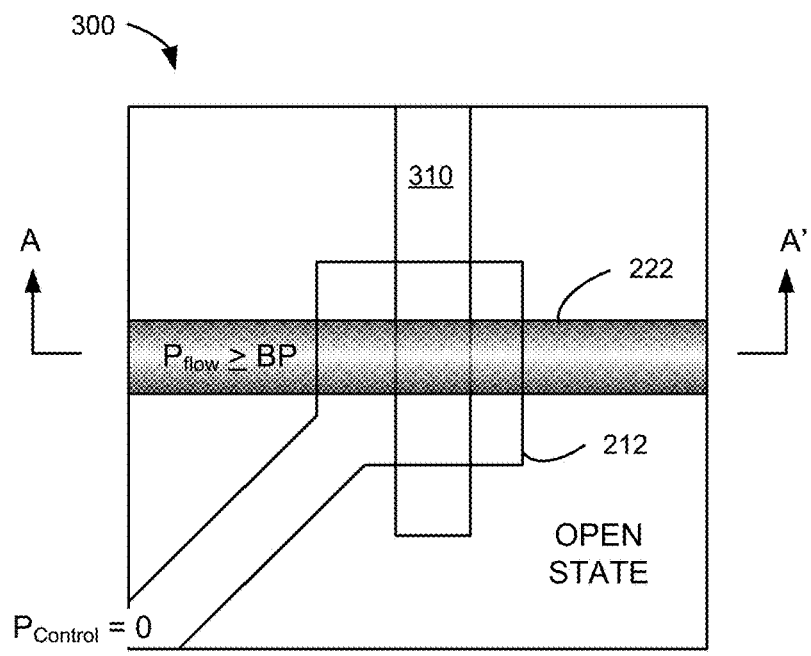
FIG. 3A is an image illustrating a static gain valve in an open condition according to an embodiment of the present invention.

FIG. 3A is a top view illustrating a static gain valve 300 in an open state or condition according to an embodiment of the present invention. As illustrated in FIG. 3A, an embodiment includes an NCV fill channel (vertical) 310, a flow channel 222 in the adjacent flow layer, and a control layer 210 in which the control membrane 214 is shaped as a rectangular feature underling the flow channel. Other geometries can be utilized and the particular structure illustrated in FIG. 3A is merely to provide an exemplary implementation.

For a flow pressure of zero in the flow channel 222, the valve is closed due to the pressure exerted by the material in the fill channel 232 to deflect the flow layer membrane 224 and result in contact between the materials on opposing sides of the flow channel 222. Assuming no pressure is applied to the control channel 212 (i.e., $P_{control}=0$), as the pressure in the flow channel increases to a value greater than or equal to the breakthrough pressure (i.e., $P_{flow} \geq BP$), the valve will open, enabling flow through the flow channel 222 as illustrated in FIG. 3A.

Figure 3B:
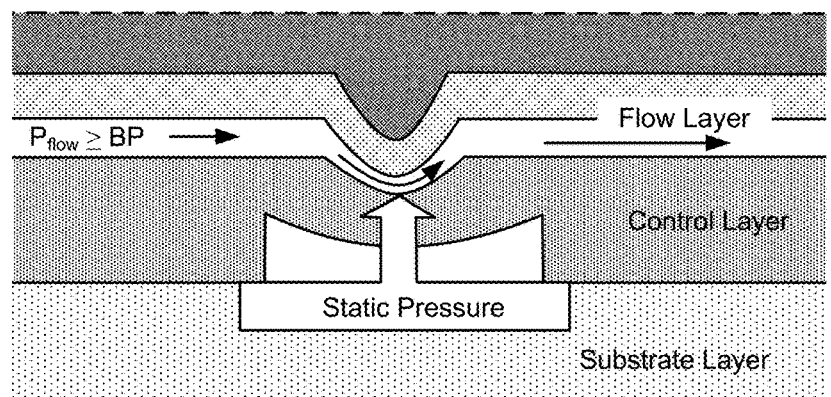
FIG. 3B is a simplified schematic diagram illustrating a cross-section of the static gain valve of FIG. 3A.

FIG. 3B is a simplified schematic diagram illustrating a cross-section of the static gain valve 200 of FIG. 3A along direction A-A'. As illustrated in FIG. 3B, since the pressure in the flow channel 222 is greater than or equal to the breakthrough pressure, the flow layer membrane deflects upwards and the valve opens, establishing flow through the flow channel. In this embodiment, the pressure applied to the control channel, which can also be referred to as the input pressure or static pressure is zero (i.e., $P_{control}=0$).

Figure 4A:
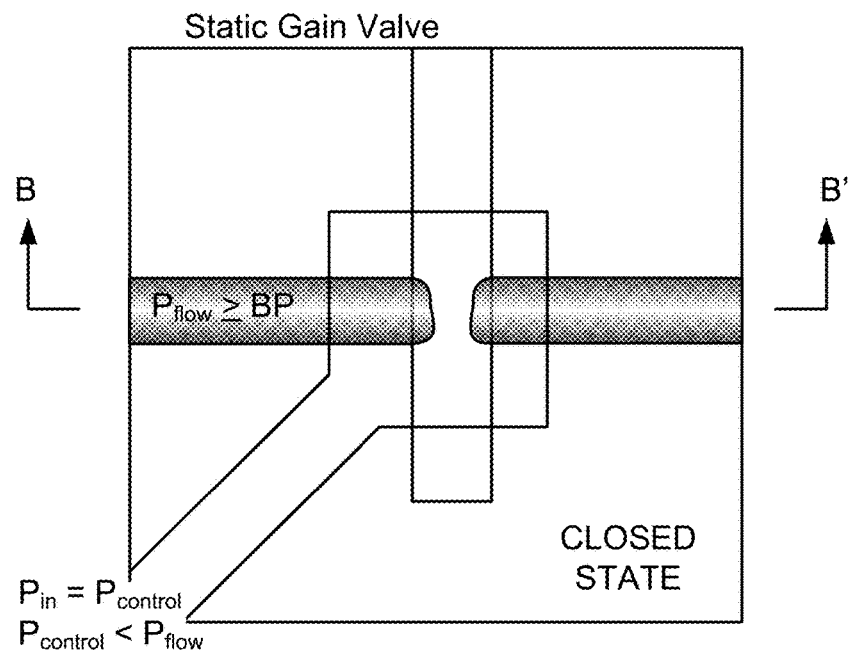
FIG. 4A is an image illustrating a static gain valve in an closed condition according to an embodiment of the present invention.

FIG. 4A is an image illustrating a static gain valve in an closed condition according to an embodiment of the present invention. As illustrated in FIG. 4A, a pressure of $P_{control}$ has been applied to the control channel, resulting in a pressure in the control channel of $P_{control}$+Static Pressure gain/differential. In the illustrated embodiment, the control pressure is less than the pressure in the flow channel (i.e., $P_{control} < P_{flow}$). As will be evident, in the closed state, the control pressure in the control channel is greater than atmospheric pressure.

Figure 4B:
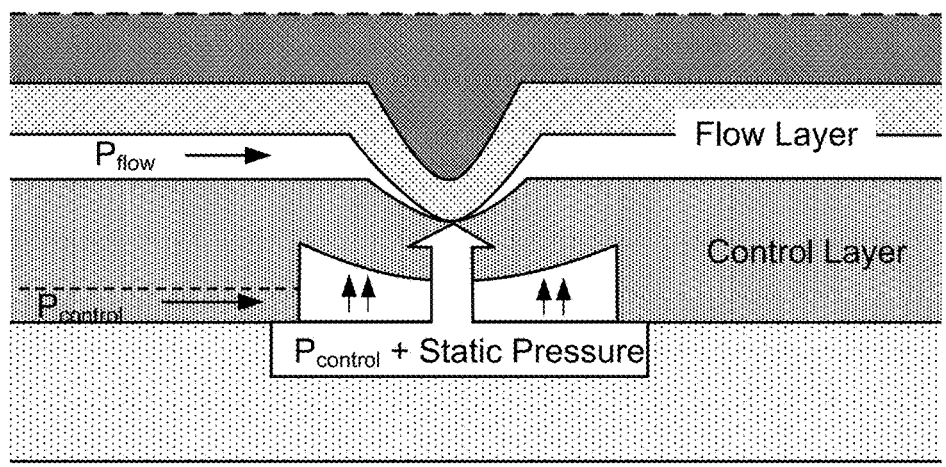
FIG. 4B is a simplified schematic diagram illustrating a cross-section of the static gain valve of FIG. 4A.

FIG. 4B is a simplified schematic diagram illustrating a cross-section of the static gain valve of FIG. 4A. The input pressure applied to the control channel ($P_{in}=P_{control}$) deflects the control membrane towards the flow layer membrane, constricting the flow channel and closing the valve, which is illustrated by the lack of fluid in the central portion of the flow channel in FIG. 4A. As illustrated in these figures, the pressure used to close the valve ($P_{in}=P_{control}$) is less than the pressure in the flow channel ($P_{flow}$).

As discussed above, during the fabrication process, the static gain of the valve can be increased by increasing the breakthrough pressure using a higher fill line pressure during the fabrication of the static gain valve, which results in an increased pressure with which the flow layer membrane is deflected towards the control membrane. Thus, the static pressure is always present and acts against the pressure exerted by the fluid in the flow channel (i.e., $P_{flow}$). When a pressure is applied to the control channel input (i.e., $P_{control}$) and thereby to the control layer membrane, the pressure exerted on the valve is the sum of input pressure (i.e., $P_{control}$) plus the built-in pressure (Static Pressure) as illustrated in FIG. 4B/Thus, using embodiments of the present invention, a smaller control pressure ($P_{control}$) applied to the control layer membrane can be used to close the valve at control pressure levels less than the pressure in the flow channel, effectively rendering the flow channel discontinuous. Because a smaller input pressure can be used to control a larger output pressure, the valve exhibits static gain.

As described more fully herein, because the valve includes logic properties including gain, the valve provided by embodiments of the present invention can be used in constructing logic gates such as NOT, NOR, NAND, and other suitable gates, an oscillator, a gated flip-flop (latch), a delay flip-flop, and a serial-in, parallel-out shift register, pumps, autonomous pumps, and the like. Embodiments of the present invention are not limited to these particular logic devices and other logic devices included within the scope of the present invention are described in U.S. Pat. No. 6,802,342, the disclosure of which is hereby incorporated by reference in its entirety for all purposes.

Referring to FIG. 4B, the static gain valve (MGV) includes a normally closed valve equipped with a flexible control layer membrane that is used to modulate the breakthrough pressure of the valve. The static gain valve utilizes the principle of pressure summation, i.e., the built-in breakthrough pressure provides the valve with static pressure (SP) by acting in conjunction with the input pressure (making the effective membrane control pressure ≈ input control pressure+static pressure). The pressure difference between the pressure in the flow layer ($P_{flow}$) and the pressure that is sufficient to control that flow is approximately constant and can be referred to as the static gain, the multiplicative gain, or the differential gain. In contrast with normally open valves, which utilize a higher (input) control pressure than the flow pressure, a static gain valve can control higher flow pressures using smaller control pressures: $P_{flow} \geq P_{control}+SP$. The performance characteristics of a static gain valve can be measured by measuring the input control pressure used to control higher flow pressures and identifying the ratio of flow pressure to control pressure as the static gain (i.e., Static Gain=$P_{flow}/P_{control}$). The static gain of the valve can be tuned by controlling the breakthrough pressure of the normally closed valve and can be accomplished by controlling the fill line pressure or by modifying the geometry of the valve. As an example, if the flow pressure ($P_{flow}$) is 15 psi and the static pressure (SP) is 10 psi, then a control pressure ($P_{control}$) of 5 psi could be used to close the valve, resulting in a static gain of 3.0.

Figure 5:
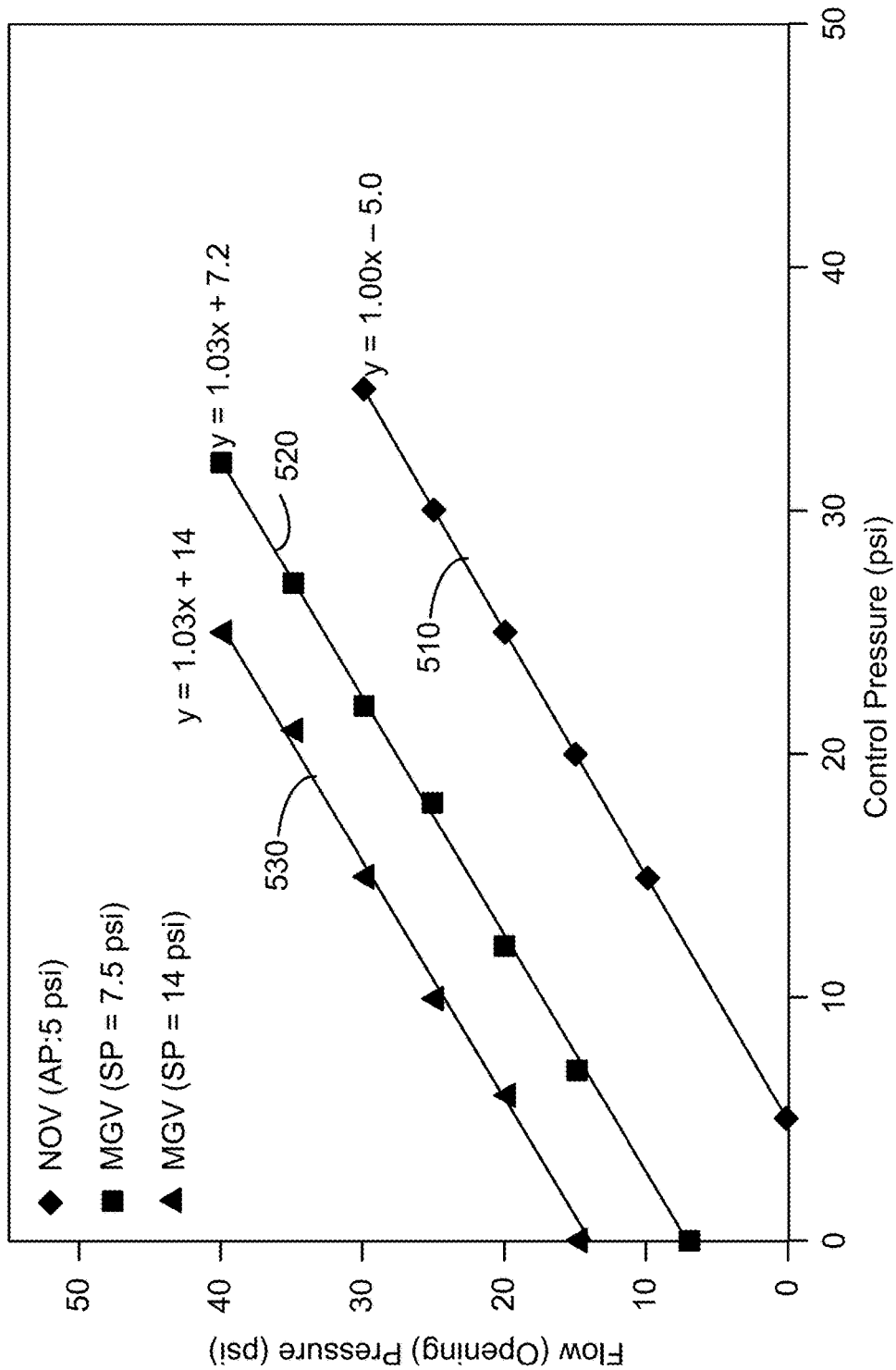
FIG. 5 is a simplified plot illustrating flow pressure versus control pressure for valves according to an embodiment of the present invention.

As an example, a static gain valve was fabricated utilizing a 100 μm×100 μm NCV controlled by 300 μm×300 μm control layer membrane. FIG. 5 is a simplified graph illustrating flow pressure at opening of the valve versus control pressure for the valve according to an embodiment of the present invention. Referring to FIG. 5, a normally open valve (NOV) is illustrated as plot 510 with a slope of unity and a control pressure of 5 psi used to close the valve (i.e., Actuation Pressure (AP)=5 psi). Plots for two static gain valves, with a static pressure of 7.5 psi and 14 psi, respectively, are also illustrated in FIG. 5 as plots 520 and 530. As shown in FIG. 5, at a flow pressure of 20 psi, each of the static gain valves utilize a control pressure of 12 psi and 6 psi, respectively, resulting in static gain equivalents of 1.66 and 3.33, respectively. Thus, using normally closed valves, static gain valves are provided that allow a higher pressure to be controlled by a lower pressure (i.e., a static gain equivalent). The static gain valve can be used as a ON-OFF switch or gate. In an embodiment, when the gate is "closed," the flow through the flow channel is disrupted and the switch is set to "OFF" state. When the gate is "open," the operation switches so that the fluid is flowing in a "pass through" or "ON" state.

Referring to FIG. 5, the slope for each of the plots, for both the normally open valve (NOC) as well as the static gain valves (MGV) is approximately unity, indicating that no static gain is provided by these valves. However, for the MGVs, a static gain equivalent is provided by the ratio of the flow pressure (i.e., output pressure) to the control pressure (i.e., input pressure).

Utilizing the static gain valves described herein, a number of logic gates and logical devices are implemented. As an example, an inverter (NOT gate) is fabricated. The NOT gate can then be used to fabricate more complex circuits including fully cascadable fluidic logic circuits powered by fluid pressure such as NAND gates, NOR gates, other logic gates, bi-stable flip flops, clocked flip flops (latches), delay flip flops, oscillators, complex microprocessor (e.g., shift registers), and self feeding single input peristaltic pumps (e.g., utilizing the NOT gate). The logic devices described herein implement binary logic and adhere to Boolean rules. Devices receive either a "1" (pressure above atmospheric pressure) or a "0" (atmospheric pressure) as the input. The circuits can use air or liquid as the medium for signal transfer. Circuits are powered by a common pressure source, S (e.g., a large capacity channel serving as a pressure reservoir connected to an external pressure source) and ground terminals are connected to a common drain, D (e.g., a vent to atmosphere), which are fluidic analogues to a source and a sink. As will be evident to one of skill in the art, a large number of complex circuits can be built utilizing a NOT gate.

FIG. 6A is a simplified schematic diagram of a NOT gate according to an embodiment of the present invention. FIG. 6B is a plan view of a NOT gate with a "1" or "HIGH" input applied to the control channel according to an embodiment of the present invention and FIG. 6C is a plan view of a NOT gate with a "0" or "LOW" input according to an embodiment of the present invention. As illustrated in FIG. 6A, an input 610 applied to the control channel (i.e., a gate of the logic device) of the NOT gate is inverted at the output 620 of the NOT gate using the membrane controlled normally closed MGV 605. As shown in FIG. 6B, an input channel 615 connected to the pressure source (S) on one end is equivalent to a Source and an output channel 616 on the other end (Drain) is connected to atmospheric pressure, separated by the intervening static gain valve. The control input is "ON" or "1" in FIG. 6B. For this control input 610, the MGV is placed in the closed state and the output 620 is atmospheric pressure (a "0" or "OFF" output) since the drain of the NOT gate is tied to atmospheric pressure (represented by a ground symbol).

When the control input 610 to the inverter is supplied with "0" (i.e., atmospheric pressure) as illustrated in FIG. 6C, the gain valve is set to the "pass through" or open state as it is pushed open by the pressure present at the Source, connecting the output 620 to the Source so that the output pressure becomes substantially equal to the Source pressure (i.e., a "1"). The Source is in fluid communication with an input reservoir, also referred to as an input source characterized by a source pressure, through a via passing from the input channel to the fill channel of the fill layer at a portion of the fill channel that was not filled with the fill material. When the control input 610 is changed back to a "1," the valve closes, disconnecting the output 620 from the source and thereby reducing the pressure to atmospheric pressure (i.e., "0") by venting the fluid out through the drain, which is connected to atmosphere by a channel that is characterized by a high resistance to fluid flow. In some embodiments, the output 620 is a channel that is used to control the next gate in the logic device. It should be noted that the control input is a pressure that is distinct from the input channel (Source), which is present at the output channel (Drain) in the inverted state. Thus, although the terms "HIGH" and "LOW" and the like are used herein, it will be appreciated that a "HIGH" pressure for the control signal is not necessarily equal to a "HIGH" pressure for the output channel, which is substantially equal to the pressure in the input channel.

Referring to FIG. 6B, because the output at the drain is "0" or "LOW," the valves V1 and V2, which are connected to the output, are open. In contrast, in FIG. 6C, because the output at the drain is "1" or "HIGH," the valves V1 and V2 are closed. Thus, the control signal applied to the MGV is operable to operate the downstream valves.

As illustrated in FIGS. 6A-6C, the output signal strength of the NOT gate is related to the common pressure source connected to the Source and is substantially equal to the source pressure. Because of the benefits provided by the designs described herein, the input signal is thus refreshed at each output channel, resulting in substantially no loss of signal strength in a cascade of gates. Thus, embodiments of the present invention are suitable for use in fabricating elaborate and/or complex logic circuits, for which it is desirable to have no accumulation of signal loss during signal transportation in a cascade. Accordingly, pressure at the output of the NOT gate is at full strength (compared to the source pressure) irrespective of the drain resistance in some embodiments providing for unlimited cascadability in some embodiments.

In some implementations, the flow rate through the drain is lower than the flow rate through the gain valve into the output arm. As a result, switching times from the 0 to the 1 state may be different than switching times from the 1 state to the 0 state. In the implementation illustrated in FIG. 6A, the switching time for the transition from the 1 state to the 0 state is dependent on the resistance from the drain to ground, which can impact the speed at which a device functions. One of ordinary skill in the art would recognize many variations, modifications, and alternatives.

FIG. 7A is a simplified schematic diagram of a NOR gate according to an embodiment of the present invention. FIG. 7B is an image of a NOR gate with a single "1" input according to an embodiment of the present invention and FIG. 7C is an image of a NOR gate with two "0" inputs according to an embodiment of the present invention. The two NCVs connected in series as illustrated in FIG. 7A provide a NOR functionality in which a high output (1) results if both the inputs to the gate are low (0) and if one or both inputs are high (1), a low output (0) results. As illustrated in FIG. 7B, one of the controls or inputs (IN1) is "OFF" (0) and one of the controls or inputs (IN2) is "ON" (1), resulting in the output being "OFF." In FIG. 7C, both inputs are "OFF" (0), resulting in the output being "ON." If both inputs were "ON," then the pressure connected to the source would be produced at the output, producing an "OFF" output.

FIG. 8A is a simplified schematic diagram of a NAND gate according to an embodiment of the present invention. FIG. 8B is an image of a NAND gate with both inputs set at a high value "1" according to an embodiment of the present invention and FIG. 8C is an image of a NAND gate with a single "1" input according to an embodiment of the present invention. The two NCVs connected in parallel as illustrated in FIG. 8A provide a NAND functionality in which a high output (1) results if one or both inputs are high (1), and a low output (0) results if both the inputs to the gate are high (1). As illustrated in FIG. 8B, both of the inputs (IN1 and IN2) are "ON" (1), resulting in the output being "OFF." In FIG. 8C, one of the inputs (IN1) is "ON" (1) while the other input (IN2) is "OFF" (0), resulting in the output being "ON."

Although only NOT, NOR, and NAND gates are illustrated in relations to FIGS. 6A-8A, embodiments of the present invention are not limited to these particular gates and other logic devices incorporating the NCV described herein are included within the scope of the present invention. As examples, and without limiting the scope of the present invention, oscillators, clocked flip flops, latches, and the like are included within the scope of the present invention. Embodiments of the present invention provide the capability to build microfluidic logic devices into microfluidic devices, enabling control of sections of the microfluidic devices based on the inputs and outputs of the control logic. As an example, a portion of the microfluidic device could be activated or deactivated by control logic, computations could be performed and the results used in controlling processes performed on the microfluidic device. One of ordinary skill in the art would recognize many variations, modifications, and alternatives.

Figure 9A:
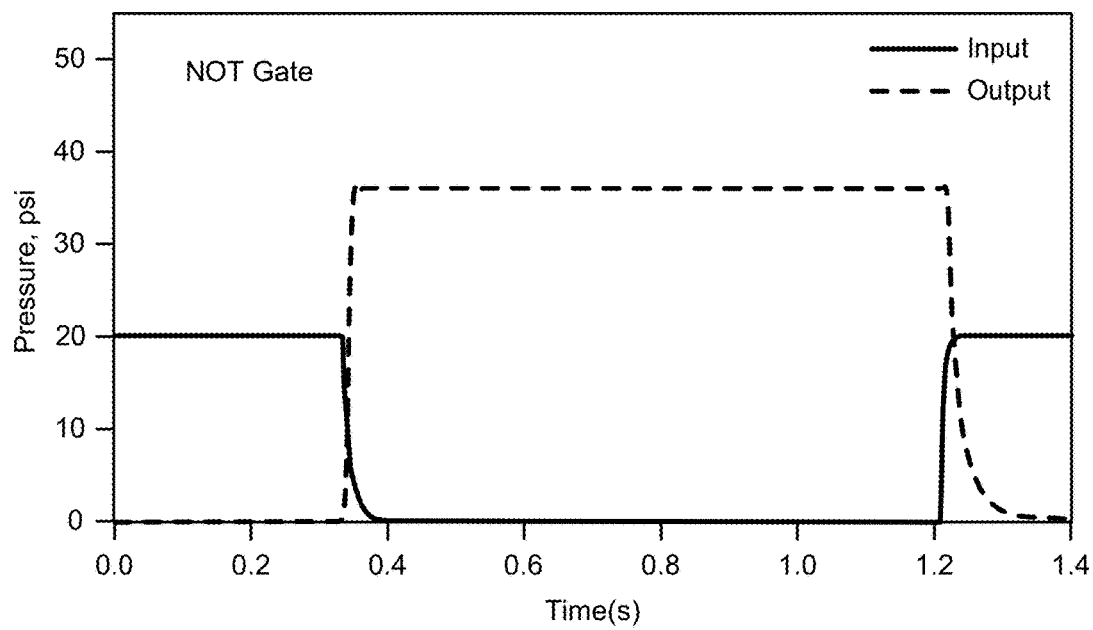
FIG. 9A is a simplified timing diagram for a NOT gate according to an embodiment of the present invention.

FIG. 9A is a simplified timing diagram for a NOT gate according to an embodiment of the present invention. The input or control is initially at a value of 20 psi and can be referred to as HIGH, "1," "ON," or the like. As appropriate to this input, the output is initially at a value of 0 psi with respect to atmospheric pressure and can be referred to as LOW, "0," "OFF," or the like. At about 0.35 seconds, the input is switched from a high value to a low value, i.e., 0 psi. In response to the change in the input, the output switches to ~37 psi after a predetermined rise time, which is associated with a "1" or other suitable high value. The static gain is equal to about 1.85 based on the ratio of the output pressure to the input pressure. At about 1.2 seconds, the input pressure is returned to the initial value of 20 psi, resulting in the output returning to the initial value of 0 psi after a predetermined fall time.

Figure 9B:
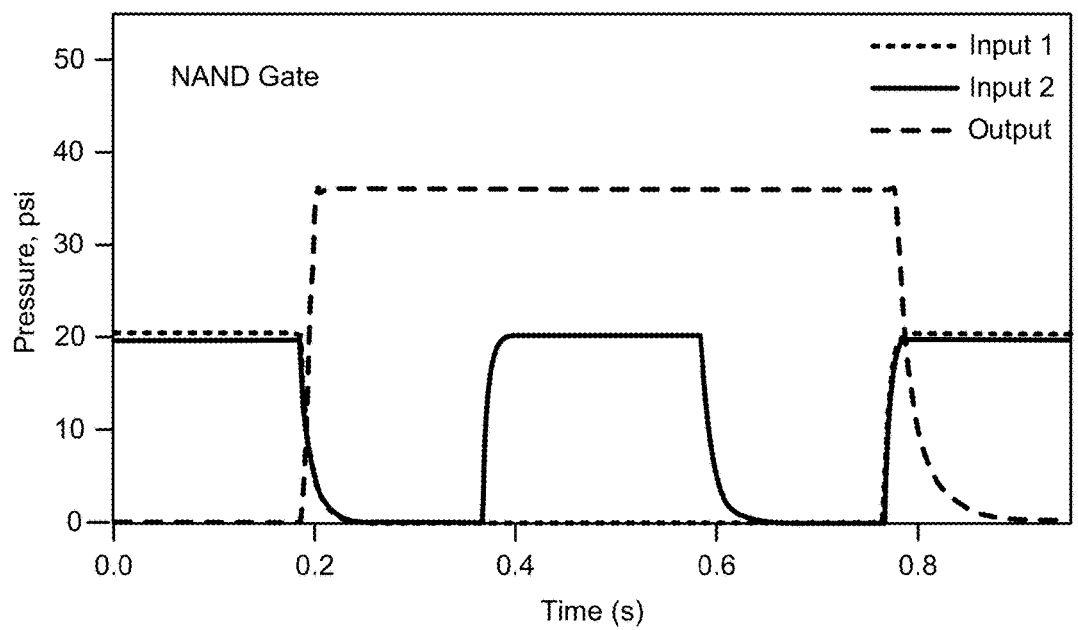
FIG. 9B is a simplified timing diagram for a NAND gate according to an embodiment of the present invention.

FIG. 9B is a simplified timing diagram for a NAND gate according to an embodiment of the present invention. Initially, the two controls or inputs for the NAND gate are HIGH (i.e., 20 psi), resulting in an output that is LOW. At about 0.2 seconds, both inputs are switched to LOW, resulting in the output switching to HIGH (i.e., ~37 psi). Although one of the inputs (Input2) is switched HIGH at about 0.37 seconds, the output remains high as appropriate for a NAND gate. When both inputs return to HIGH at about 0.77 seconds, the output switches LOW as illustrated. The static gain valves utilized in these measurements are characterized by a static pressure of 15 psi, an input pressure of 20 psi and a source pressure of 35 psi.

Utilizing embodiments of the present invention, response times from LOW to HIGH can be less than or equal to 25 ms measured at 50% of the peak pressure. The from HIGH (1) to LOW (0 or atmospheric pressure) exhibits exponential behavior and the inventors have determined that the response time can vary as a function of the resistance associated with the drain (for example, from <50 ms to >2 s).

In some implementations, pneumatically operated microfluidic circuits are utilized in place of or in conjunction with hydraulic fluidic circuits, for example, with a pneumatic control platform and conversion of the final output to hydraulic signals for the control of the valves/valve structure. This design reduces or eliminates air entrapment in the reagent chambers of the device under control. Circuit designs allow for conversion of signals from pneumatic (input) to hydraulic (output) or vice versa at any stage by switching the source for that particular gate.

As another example of a device that can be fabricated according to embodiments of the present invention, a fluidic oscillator was fabricated using a NOT gate connected in a feedback loop, with the output of the NOT gate fed back into the input through a fluidic resistor and capacitor in series. When the pressure signal is turned "ON," the signal travels through the loop and starts generating repetitive pressure pulses at a predetermined frequency. The frequency and the amplitude of the oscillator increases proportionally with the source pressure. The frequency has an inverse relation to the embedded fluidic resistor and capacitor (as normalized RC numbers). Oscillators with higher RC numbers produce lower number oscillations and lower RC numbers tend produce pulses at higher frequency.

A flip flop can be formed by combining two inverters such that the output of each serves as the input of the other. A flip flop has two stable states—buffered and inverted, and can be used to save 1 bit of information. A bi-stable flip flop was constructed using inverters and occupies an area as small as 2.4 mm$^2$, which is significantly smaller than those demonstrated using conventional designs. A gated flip-flop acts a latch and holds the state even when the input is withdrawn. Two gated flip flops (latches) connected serially with the first gate controlled by a "clock" signal and the second by inverse of the clock signal ("anti-clock") form a delay flip flop (D flip flop). A shift register capable of processing n+1 bits of information is formed when n D flip flops are connected sequentially. A shift register has 3 active inputs—(1) Clock, (2) Input (Data), and (3) Trigger. The input line receives the data serially and processes the command sequence into parallel individually addressable command bits. Data advances by one bit through the shift register with each clock cycle. A common bi-stable flip-flop supplies the clock and anti-clock signals. Turning the trigger line OFF opens the gates at the output and allows the control signals into the chip to control valves or run multiple devices. The logic devices provided by embodiments of the present invention are physically compact, with the small feature sizes and the use of positive pressures to drive the circuits resulting in high operational speeds (greater than 10 Hz), which is 20 times faster than the speed of the signal transfer in conventional pneumatic circuits.

A 12 bit shift register was fabricated, occupying ~84.5 mm². Including the associated output network the device size only increased to 150 mm². A 32 bit shift register occupies only ~400 mm² and can be integrated on a 10 cm wafer by using less than 4% of the area. Shift registers of arbitrary length can be built and run using only three active inputs—clock, data, and trigger. The shift register discussed here controls 12 independent control lines using three input signals. By using the oscillators as auto clocking devices, active control for the clock as well as the trigger can be reduced or eliminated and shift and state registers of theoretically unlimited lengths can be operated with only a 2 external control lines—source and data.

In addition to the above-referenced fluidic logic devices, the inventors have fabricated a self fed single input peristaltic pump by joining two delay flip flops and continuously circulating an output through the latches (individual gated flip flops) by feeding the output of the fourth latch into the first one. The output is drawn from all the latches to drive the pump. Single active input signal controls the clock (flip flop), which generates clock and anti clock signals. In a particular implementation, an integrated oscillator runs the pump with no active inputs. Thus, a complete set of microfluidic logic based on valves with static gain is provided by embodiments of the present invention.

The on-chip integration of control systems reduces the external devices and equipment used to operate a microfluidic device, thereby providing an opportunity to integrate and simultaneous control multiple analysis systems. While fluidic logic circuits may be slower than solid state devices, their operating speeds are fast compared to most chemical and biochemical processes, thereby offering a method of implementing handheld and/or autonomous control in microfluidic chips.

Figure 10:
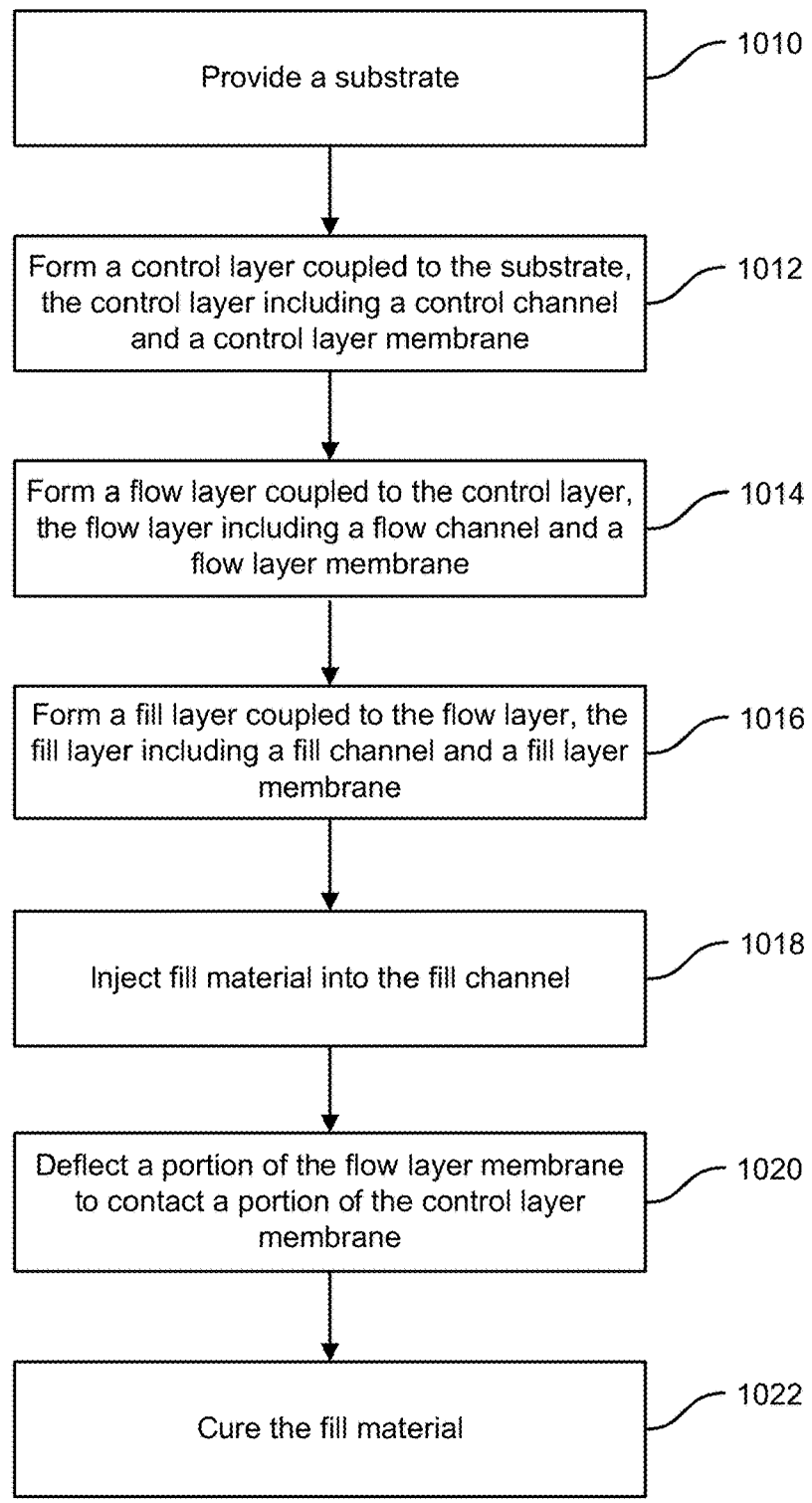
FIG. 10 is a simplified flowchart illustrating a method of fabricating a microfluidic device according to an embodiment of the present invention.

FIG. 10 is a simplified flowchart illustrating a method of fabricating a microfluidic device according to an embodiment of the present invention. The method 1000 includes providing a substrate (1010) and forming a control layer including a control channel and a control layer membrane (1012). The substrate can be one of several materials characterized by mechanical rigidity and resistance to chemical attack, including glass, plastic, PDMS, or the like. The control channel can include a chamber underlying the flow channel, with lateral dimensions greater than a lateral dimension of the flow channel, thereby enabling the control channel to apply pressure to the control layer membrane and to displace the control layer membrane toward the flow layer membrane. The method also includes forming a flow layer coupled to the control layer (1014). The flow layer includes a flow channel and a flow layer membrane. The method further includes forming a fill layer coupled to the flow layer (1016). The fill layer includes a fill channel and a fill layer membrane. In some embodiments, the control layer, the flow layer, and the fill layer are patterned in PDMS using MSL techniques such as those described in commonly assigned U.S. Pat. No. 7,666,361.

The method additionally includes injecting a fill material (e.g., an acrylate monomer) into the fill channel (1018), deflecting a portion of the flow layer membrane to make contact with a portion of the control layer membrane (1020), and curing the fill material (1022), for example, by exposure to UV radiation, heat, combinations thereof, or the like. The contact between the portion of the flow layer membrane and the portion of the control layer membrane can impede flow through the flow channel, thereby forming a valve, which can be a normally closed valve.

It should be appreciated that the specific steps illustrated in FIG. 10 provide a particular method of fabricating a microfluidic device according to an embodiment of the present invention. Other sequences of steps may also be performed according to alternative embodiments. For example, alternative embodiments of the present invention may perform the steps outlined above in a different order. Moreover, the individual steps illustrated in FIG. 10 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 12:
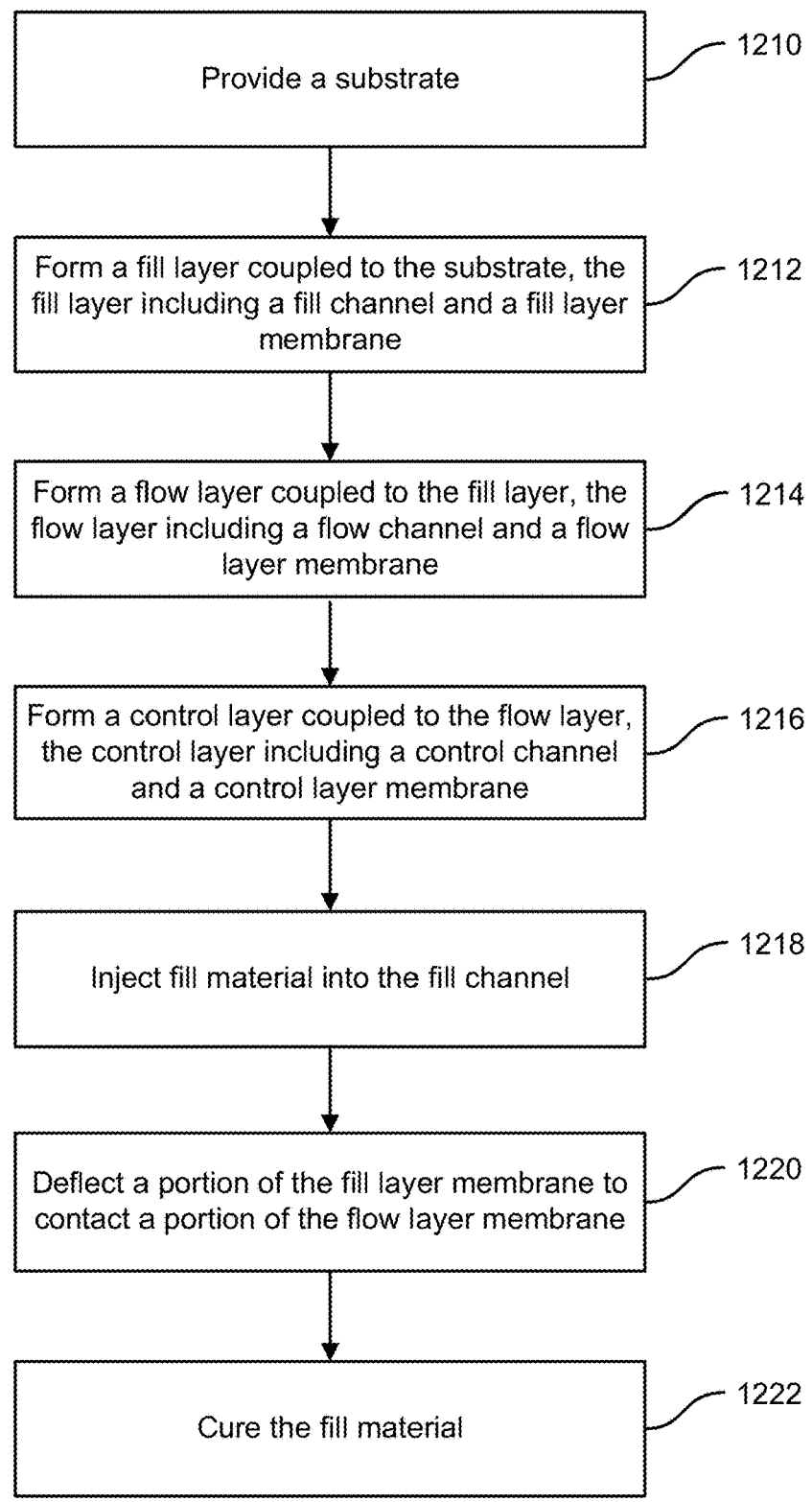
FIG. 12 is a simplified flowchart illustrating another method of fabricating a microfluidic device according to an embodiment of the present invention.

FIG. 12 is a simplified flowchart illustrating another method of fabricating a microfluidic device according to an embodiment of the present invention. The method 1200 includes providing a substrate (1210) and forming a fill layer coupled to the substrate (1212). The fill layer includes a fill channel and a fill layer membrane. The method also includes forming a flow layer coupled to the control layer (1214). The flow layer includes a flow channel and a flow layer membrane. The method further includes forming a control layer including a control channel and a control layer membrane (1216).

The method additionally includes injecting a fill material (e.g., an acrylate monomer) into the fill channel (1218), deflecting a portion of the fill layer membrane to make contact with a portion of the flow layer membrane (1220), and curing the fill material (1222), for example, by exposure to UV radiation, heat, combinations thereof, or the like. The contact between the portion of the fill layer membrane and the portion of the flow layer membrane can impede flow through the flow channel, thereby forming a valve, which can be a normally closed valve.

It should be appreciated that the specific steps illustrated in FIG. 12 provide a particular method of fabricating a microfluidic device according to another embodiment of the present invention. Other sequences of steps may also be performed according to alternative embodiments. For example, alternative embodiments of the present invention may perform the steps outlined above in a different order. Moreover, the individual steps illustrated in FIG. 12 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 11:
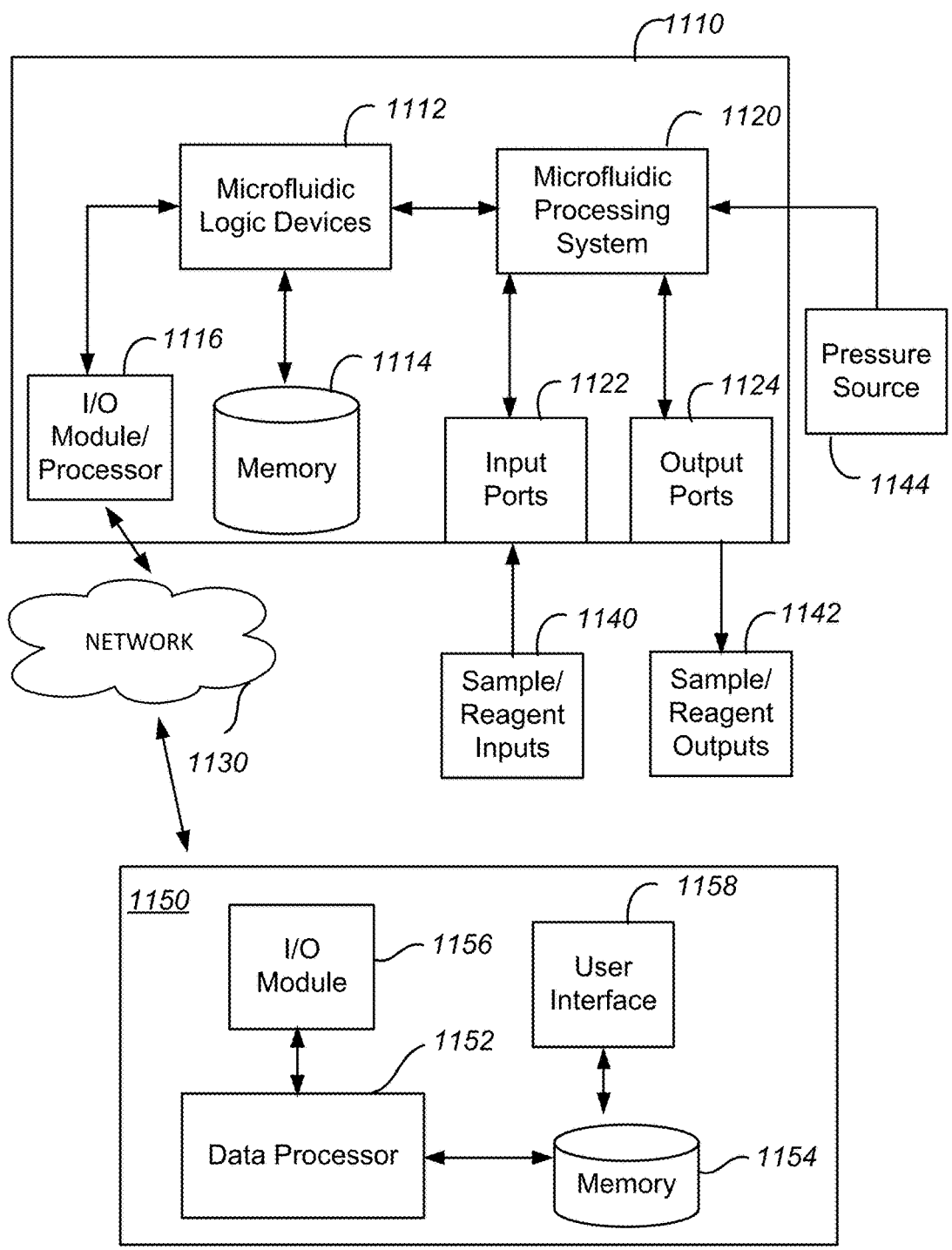
FIG. 11 is a simplified schematic diagram illustrating a microfluidic system according to an embodiment of the present invention.

FIG. 11 is a simplified schematic diagram illustrating a microfluidic system according to an embodiment of the present invention. As illustrated in FIG. 11, a user operating user computer 1150 interacts with the microfluidic system 1110 through network 1130. User computer 1150 can include one of many types of computing devices including, without limitation, a personal computer, a laptop computer, a notebook computer, a tablet computer, a handheld mobile device, a PDA, a mobile phone, or the like. The microfluidic system 1110 includes An input/output module/processor 1116 to enable communication with the microfluidic system 1110 by external users and computers. The processor can also be referred to as a data processor and is coupled to memory 1114.

The processor 1116 represents a central processing unit of any type of architecture, such as a CISC (Complex Instruction Set Computing), RISC (Reduced Instruction Set Computing), VLIW (Very Long Instruction Word), or a hybrid architecture, although any appropriate processor may be used. The processor executes instructions and includes elements suitable for control of the operation of the microfluidic system 1110. Although not depicted in FIG. 11, the processor typically includes a control unit that organizes data and program storage in memory and transfers data and other information between various elements of the system. The processor receives input data from the I/O module and the network 130, reads and stores code and data in the memory 1114, and presents data using the I/O module.

Although the illustrated embodiment is shown to contain only a single processor as part of the I/O module, the disclosed embodiment applies equally to systems that may have multiple processors. In some embodiments, a portion of the processing functions are performed by the microfluidic logic devices 1112.

The memory 1114 represents one or more mechanisms for storing data. For example, the memory, also referred to as a storage device may include read-only memory (ROM), random access memory (RAM), magnetic disk storage media, optical storage media, flash memory devices, and/or other machine-readable media. In other embodiments, any appropriate type of storage device may be used. Although only one memory 1114 is shown, multiple memories and multiple types of memories may be present. Additionally, some of the data storage functions are performed by the microfluidic logic devices 1112.

The microfluidic system 1110 also includes a plurality of microfluidic logic devices 1112 and a microfluidic processing system 1120. Utilizing the logic devices described herein, control of the processes performed using the microfluidic processing system can be controlled by the system operator. Input ports 1122 are in fluid communication with sample and reagent inputs 1140 in the illustrated embodiment although other inputs for the microfluidic processing system can be utilized in alternative embodiments. A pressure source 1144 is provided in communication with the microfluidic processing system 1120 and the microfluidic logic devices 1112. The pressure source can be used to provide actuation pressure for the valves described herein as well as other functions. Output ports 1124 are in fluid communication with sample and reagent outputs 1142. Additional description related to microfluidic processing systems is provided in commonly assigned U.S. Pat. No. 7,118,910, the disclosure of which is hereby incorporated by reference in its entirety for all purposes.

The microfluidic processing system 1120 can include control lines operable to open and close valves. Additionally, the microfluidic logic devices 1112 can be integrated with the microfluidic processing system 1120 to provide for actuation of portions of the system, opening and closing of valves to enable reagent/sample input and output flow, and the like. The on-chip logic can utilize the pressure source 1144 in operating computational and/or memory devices. One of ordinary skill in the art would recognize many variations, modifications, and alternatives.

A user operating user computer 1150 interacts with the microfluidic system 1110 through network 1130, which may be the Internet. In some embodiments, the network 1130 is partly or wholly a private wide area network, local area network, or the like. In an embodiment described in additional detail below, a user can enter an address or a search query using user interface 1158, which results in data transfer through I/O module 1156 and network 1130. The information from the user, for example, an address, can be used by the microfluidic system 1110 to process one or more chemical or biological reactions or the like. The user computer 1150 can receive responses and information from the microfluidic system 1110, process the received information using data processor 1152, store the received and/or processed information using memory 1154, and display the processed/stored information using the user interface 1158. Additional description related to user control of the microfluidic system 1110 is provided in commonly assigned U.S. Pat. Nos. 7,883,669 and 7,867,763, the disclosures of which are hereby incorporated by reference in their entirety for all purposes.

According to embodiments of the present invention, releasable check valves are fabricated using multilayer soft lithography in PDMS-based materials. In a particular embodiment, external accumulators are integrated with releasable check valves and utilized to apply pressure to microfluidic valves and channels for extended periods. In an embodiment, a normally closed valve characterized by a predetermined breakthrough pressure is utilized as a pressure accumulator. The releasable check valve incorporates a release mechanism characterized by a pressure less than the predetermined breakthrough pressure. Additional description related to releasable check valves is provided throughout the present specification and more particularly below.

In some embodiments, the releasable check valve can be considered a version of a releasable accumulator as described more fully below. Embodiments of the present invention enable the integration of accumulators into the microfluidic device, decreasing carrier size and increasing reliability.

Figure 13A:
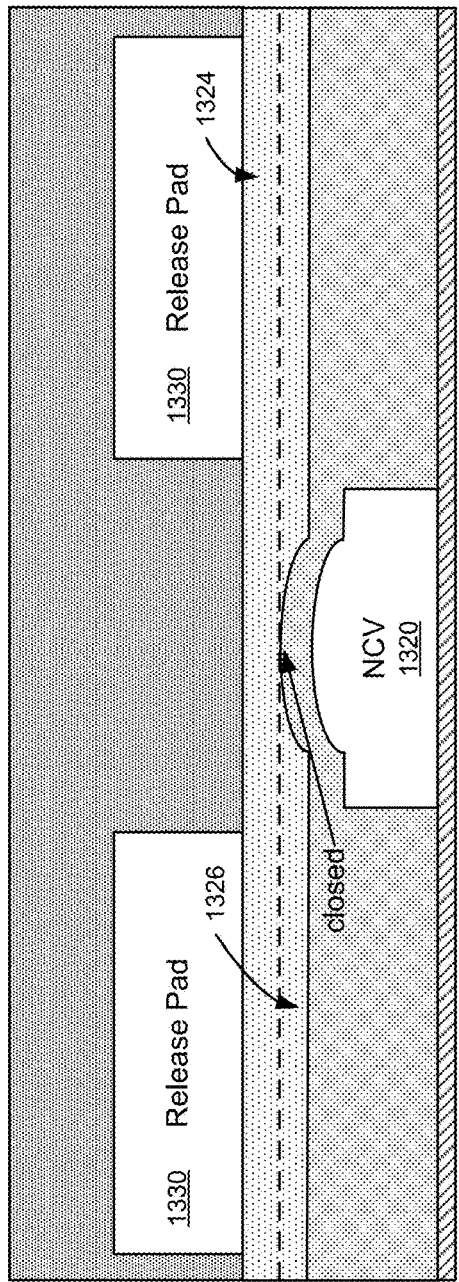
FIG. 13A is a simplified schematic diagram illustrating a releasable check valve in a closed state according to an embodiment of the present invention.

FIG. 13A is a simplified schematic diagram illustrating a releasable check valve in a closed state according to an embodiment of the present invention. The releasable check valve 1310 includes a normally closed valve (NCV) 1320 with a control membrane 1322 in contact with a flow membrane 1324, blocking fluid flow through flow channel 1326. Additional description related to the NCV is provided throughout the present specification. Although some embodiments are discussed in relation to check valves, embodiments of the present invention include valves that allow for bi-directional flow. It will be appreciated that, in general, check valves have fluid flowing in one direction. Embodiments of the present invention provide releasable check valves that allow for flow in both directions (e.g., in and out) through the valve. Thus, the releasable check valves here provide functionality not available using conventional check valves.

In addition to the elements of the NCV structure described previously, the releasable check valve 1310 also includes one or more release chambers 1330 disposed in a layer mechanically coupled to the flow membrane 1324. The release chambers 1330 are in fluid communication with release channels (not shown) that are illustrated in FIG. 13D.

Figure 13B:
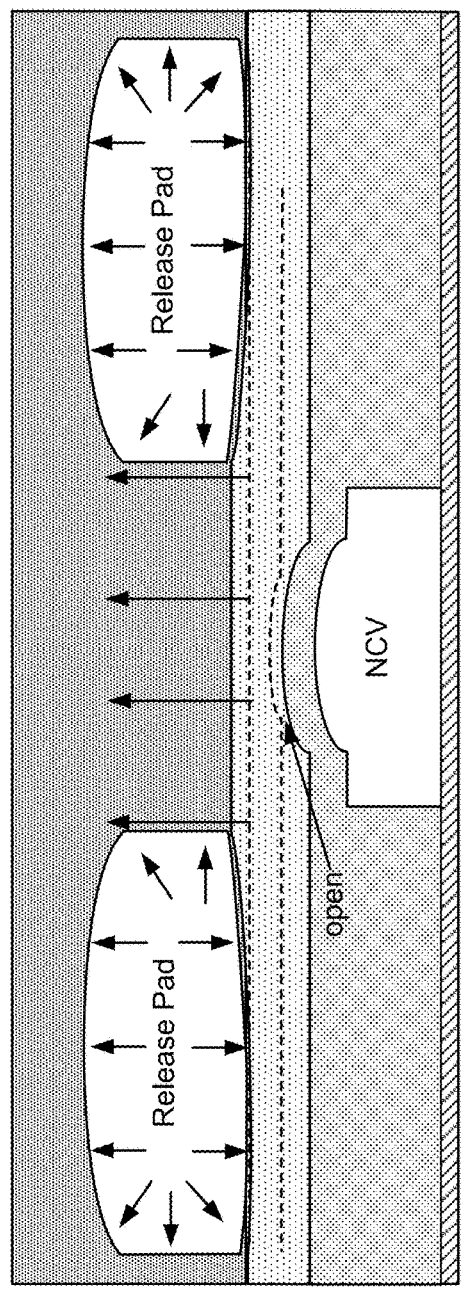
FIG. 13B is a simplified schematic diagram illustrating the releasable check valve shown in FIG. 13A in an open state according to an embodiment of the present invention.

FIG. 13B is a simplified schematic diagram illustrating the releasable check valve shown in FIG. 13A in an open state according to an embodiment of the present invention. Application of pressure to the release chambers 1330 through release channels results in contraction of the flow membrane in a direction away from the NCV, breaking the contact between the control membrane and the flow membrane, and opening the flow channel 1326. Thus, the contact between the control membrane and the flow membrane is not only dependent on the control pressure applied to the NCV and the structural parameters of the NCV, but also dependent on the pressure associated with the release chambers 1330. The actuation of the release chambers and the contraction of the flow membrane can be considered as effectively decreasing the breakthrough pressure of the NCV, enabling opening of the NCV at lower pressures than experienced when the release chambers are not pressurized.

Figure 14A:
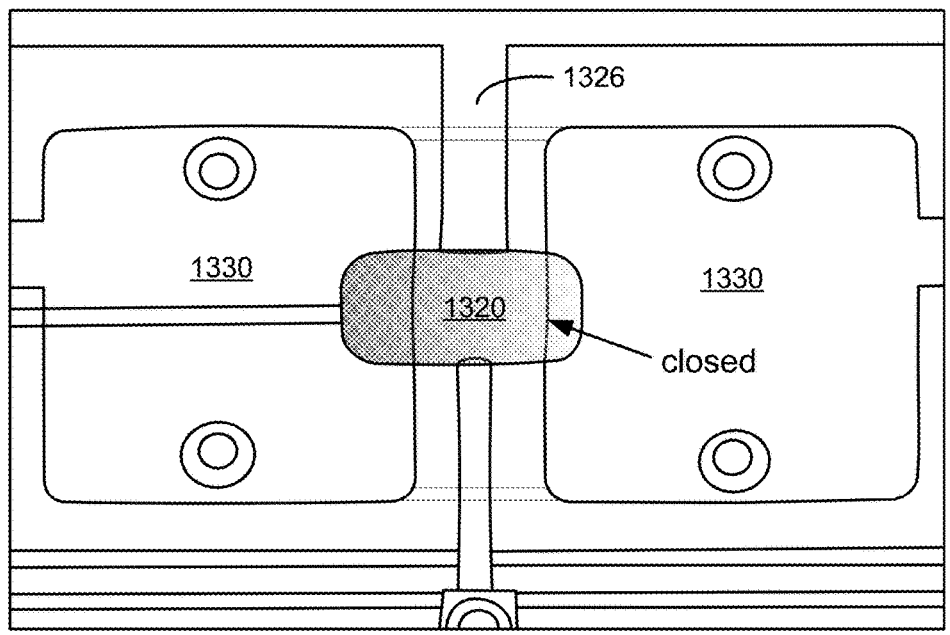
FIG. 14A is a diagram illustrating the releasable check valve in the closed state shown in FIG. 13A according to an embodiment of the present invention.

FIG. 14A is a diagram illustrating the releasable check valve in the closed state shown in FIG. 13A according to an embodiment of the present invention. As illustrated in the top view shown in FIG. 14A, NCV 1320 prevents fluid flow through flow channel 1326.

Figure 14B:
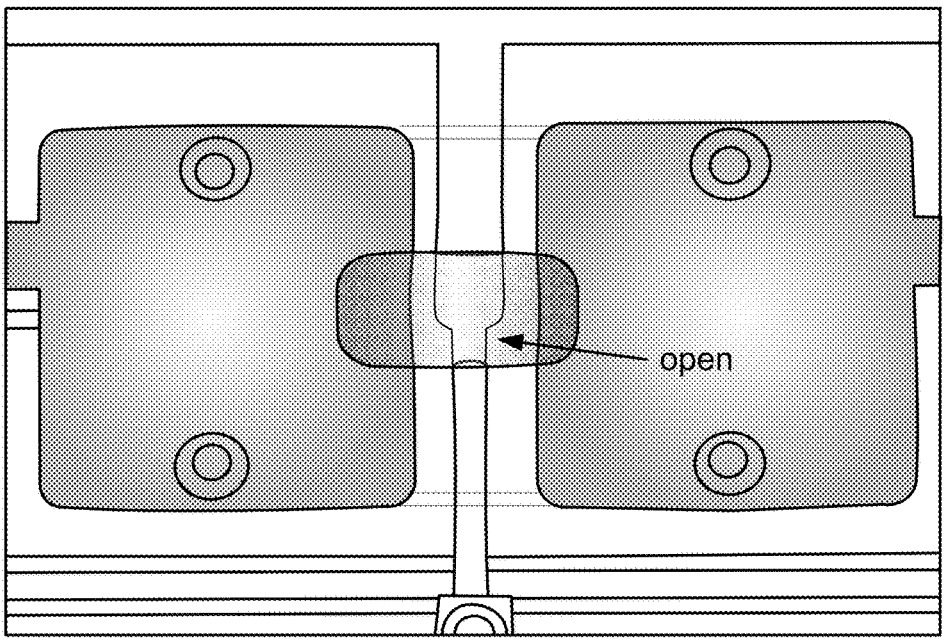
FIG. 14B is a diagram illustrating the releasable check valve in the open state shown in FIG. 13B according to an embodiment of the present invention.

FIG. 14B is a diagram illustrating the releasable check valve in the open state shown in FIG. 13B according to an embodiment of the present invention. Upon actuation of the release pads 1330, NCV 1320 opens, enabling fluid flow through flow channel 1326.

Figure 15A:
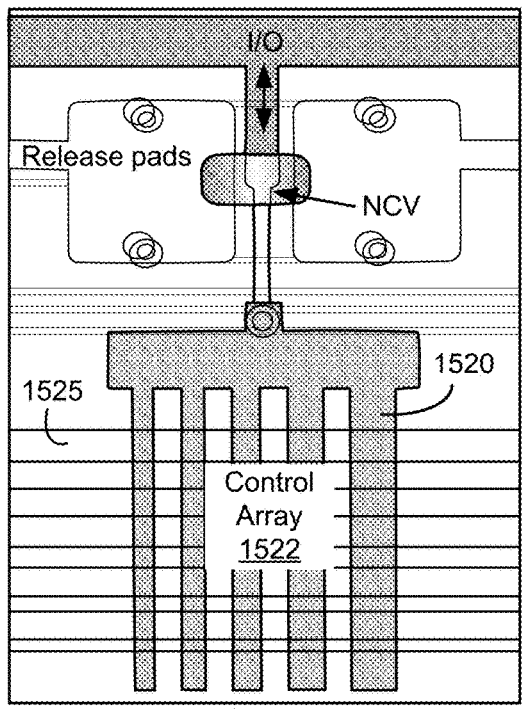
FIG. 15A is a simplified schematic diagram illustrating a releasable check valve and a control array during actuation according to an embodiment of the present invention.

FIG. 15A is a simplified schematic diagram illustrating a releasable check valve and a control array during actuation according to an embodiment of the present invention. The application of pressure greater than the breakthrough pressure in the Input/Output (I/O) channel 1510 results in opening of the NCV and pressurization (also referred to as loading) of the control lines 1520. As illustrated in FIG. 15A, the control lines 1520 are arrayed to form a control array 1522 crossing fluid lines 1525. As illustrated, the pressure on the I/O channel is sufficient to overcome the breakthrough pressure of the NCV and the fluid flows through the NCV and pressurizes the control array.

Figure 15B:
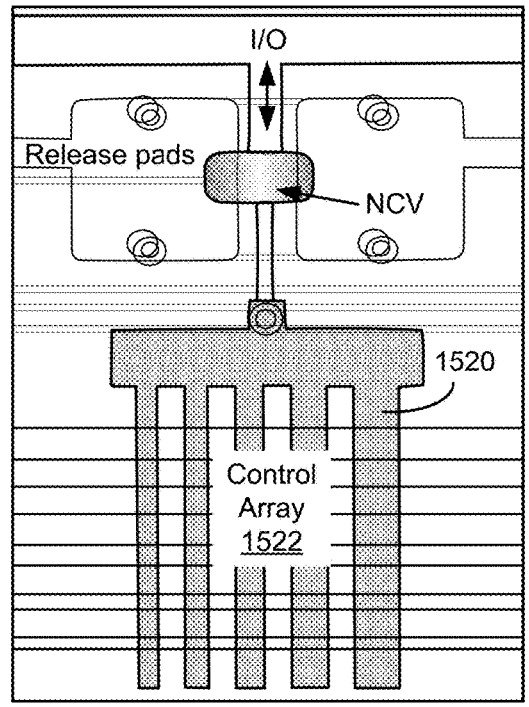
FIG. 15B is a simplified schematic diagram illustrating the releasable check valve and the control array in an actuated state according to an embodiment of the present invention.

FIG. 15B is a simplified schematic diagram illustrating the releasable check valve and the control array in an actuated state according to an embodiment of the present invention. As illustrated in FIG. 15B, although the pressure on the I/O channel 1510 has been reduced, the releasable check valve maintains the pressure on the control array 1522. The pressurization of the control array can be used to close fluid lines 1525 for a predetermined time period, without the need to maintain the pressure on the I/O channel.

Figure 15C:
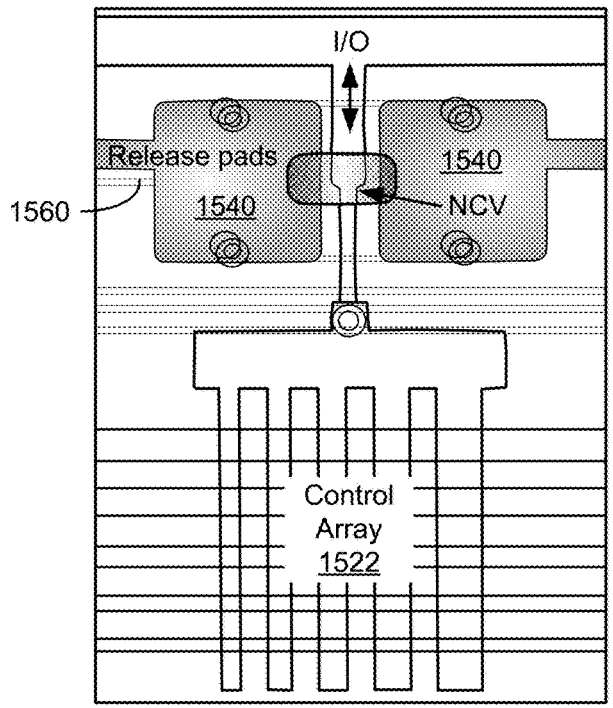
FIG. 15C is a simplified schematic diagram illustrating the releasable check valve and the control array in a released state according to an embodiment of the present invention.

FIG. 15C is a simplified schematic diagram illustrating the releasable check valve and the control array in a released state according to an embodiment of the present invention. In FIG. 15C, the release pads (also referred to as release chambers) 1540 are actuated by application of pressure to release channels 1560 in fluid communication with the release chambers, opening the NCV and enabling the fluid trapped in the control array to flow into the I/O channel 1510. As a result, the pressure on the fluid lines 1525 is reduced, enabling the resumption of fluid flow therein. Thus, embodiments of the present invention provide releasable check valves that can be used to pressurize control lines as a result of pressurization of an I/O channel, maintain the control line pressure for a predetermined period of time despite a decrease in the pressure of the I/O channel, and then release the pressure in the control lines in a reversible manner. As illustrated in FIG. 15C, the application of pressure to the release chambers effectively reduces the breakthrough pressure of the NCV, enabling the pressure present in the control array to force the NCV open, enabling fluid flow from the control array to the I/O channel.

In the embodiment illustrated in FIGS. 15A-15C, the I/O channel provides for both input and output functions, but this is not required by embodiments of the present invention.

Figure 16A:
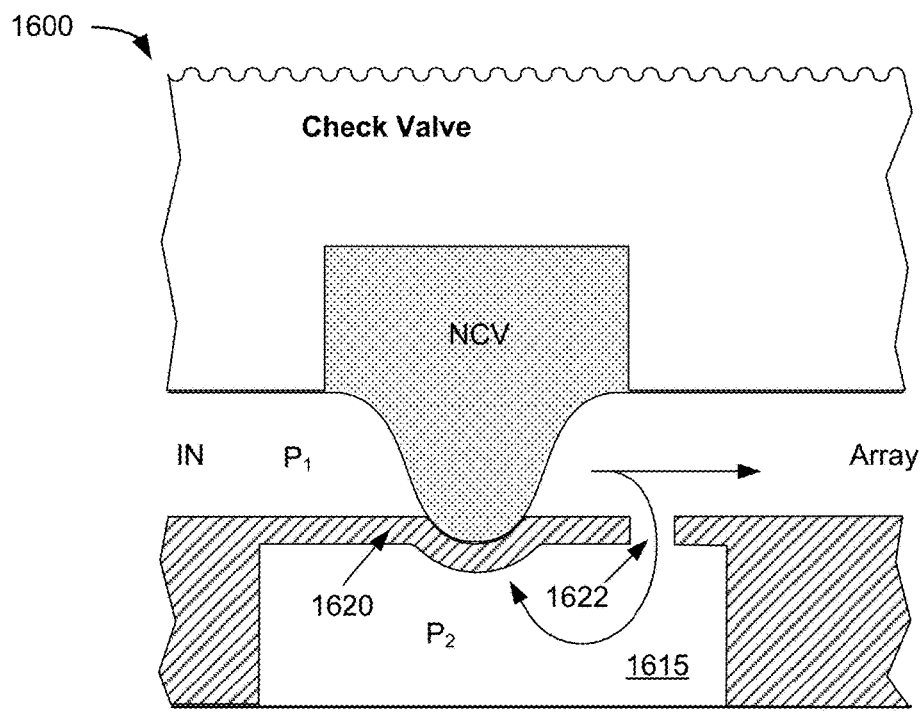
FIG. 16A is a simplified schematic diagram illustrating a check valve according to an alternative embodiment of the present invention.

FIG. 16A is a simplified schematic diagram illustrating a check valve 1600 according to an alternative embodiment of the present invention. The normally closed valve (NCV), which can be provided according to designs described herein, provides for closure of the flow channel with an input (IN) and an output (Array). The output is in fluid communication with a chamber 1615 underlying the NCV in the illustrated embodiment and separated from the NCV by a control membrane 1620. The output and the chamber are fluidly coupled through orifice 1622, which can be fabricated as a set of vias connecting a flow channel and is not limited to the single orifice illustrated in FIG. 16A. Thus, as the pressure on the input increases to the opening pressure, the pressure on the output will also increase, resulting in closing of the check valve.

In operation, when the pressure applied to the input of the flow channel exceeds the breakthrough pressure of the NCV, fluid will flow in the flow channel from the input to the output, both pressuring the array as well as the chamber 1615. The check valve will be in a closed state when the pressure at the input (IN) id equal to the pressure at the output (Array). When the pressure at the input exceeds the pressure at the output by the breakthrough pressure of the NCV, the check valve will open. The structure of the check valve includes the NCV so that when pressures are equal on either side of the NCV, the check valve is closed. Additionally, pressure on the output greater than the input ($P_{Array} > P_{IN}$) will result in the check valve being in the closed state.

Figure 16B:
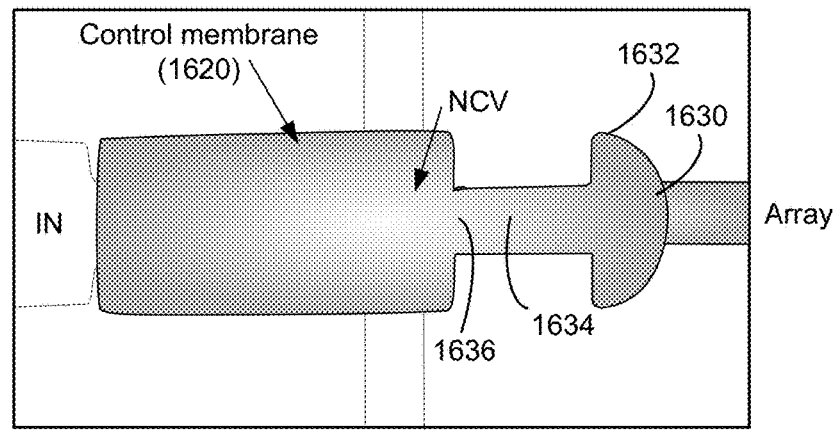
FIG. 16B is a diagram illustrating the check valve in the closed state shown in FIG. 16A according to an embodiment of the present invention.

FIG. 16B is a diagram illustrating the check valve in the closed state shown in FIG. 16A according to an embodiment of the present invention. The input channel (IN) and the output channel (Array) are illustrated as well as the control membrane 1620. A via 1630 passes from the output channel to a chamber 1632 and a flow channel 1634 connected to a second chamber 1636 underlying the control membrane and in fluid communication with the chamber 1615.

Figure 16C:
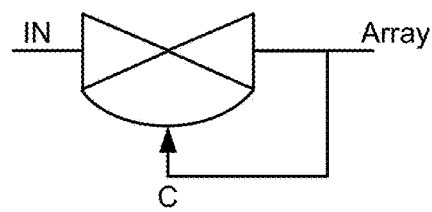
FIG. 16C is a circuit schematic for the check valve illustrated in FIG. 16A according to an embodiment of the present invention.

FIG. 16C is a circuit schematic for the check valve illustrated in FIG. 16A according to an embodiment of the present invention. The circuit includes an input IN and an output Array. The pressure at the output is present at the control C of the valve.

Figure 16D:
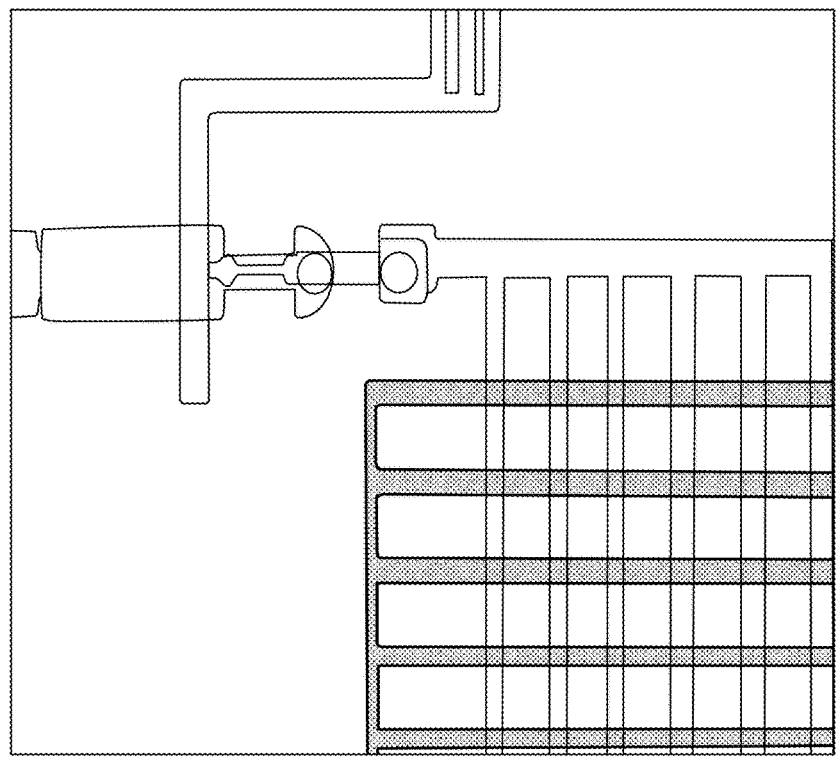
FIG. 16D is a diagram illustrating the check valve shown in FIG. 16A in a release state and a control array according to an embodiment of the present invention.

FIG. 16D is a diagram illustrating the check valve shown in FIG. 16A in a closed state and a control array according to an embodiment of the present invention. The pressure at the input is less than that required to open the NCV and the output is at a pressure associated with the closed state. In some embodiments, the output is connected to atmosphere through a high resistance fluid line, enabling the pressure in the output channel to decrease as a function of time.

Figure 16E:
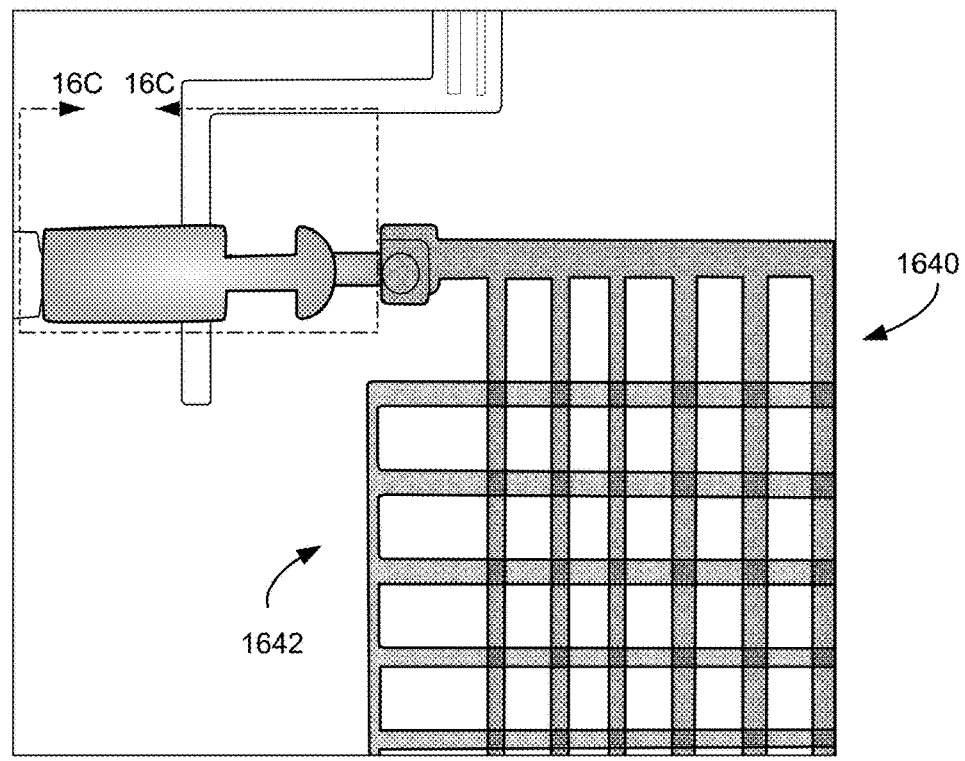
FIG. 16E is a diagram illustrating the check valve shown in FIG. 16A in a closed state and a control array according to an embodiment of the present invention.

FIG. 16E is a diagram illustrating the check valve shown in FIG. 16A in an open state and a control array according to an embodiment of the present invention. As the pressure at the input increases to a level suitable for opening the NCV, the pressure at the output becomes equal to the input pressure, pressurizing the control array 1640, which can be used to close control valves crossing fluid channels in array 1642.

Figure 17A:
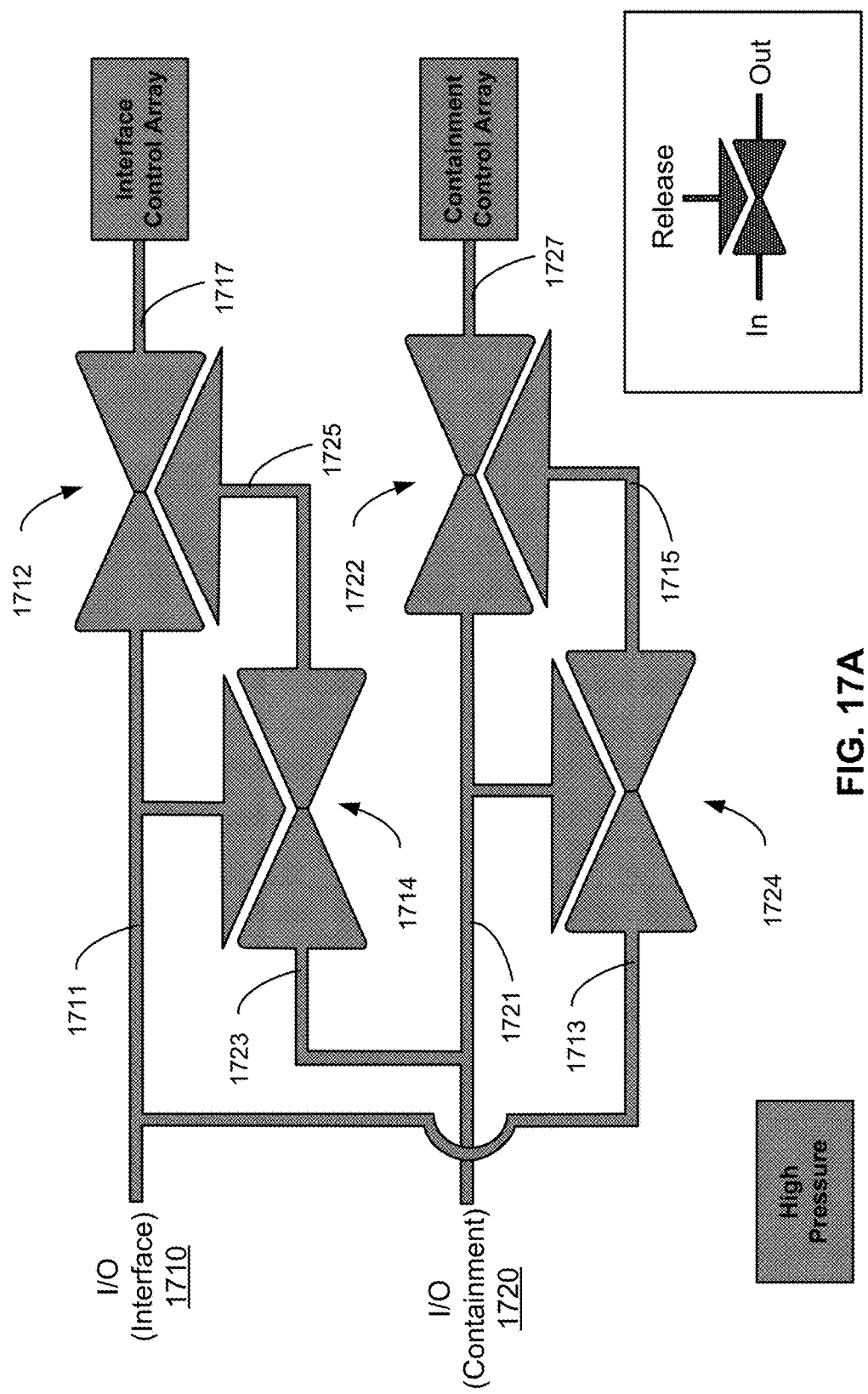
FIGS. 17A-17C are simplified schematic diagrams illustrating priming of a microfluidic array according to an embodiment of the present invention.
Figure 17B:
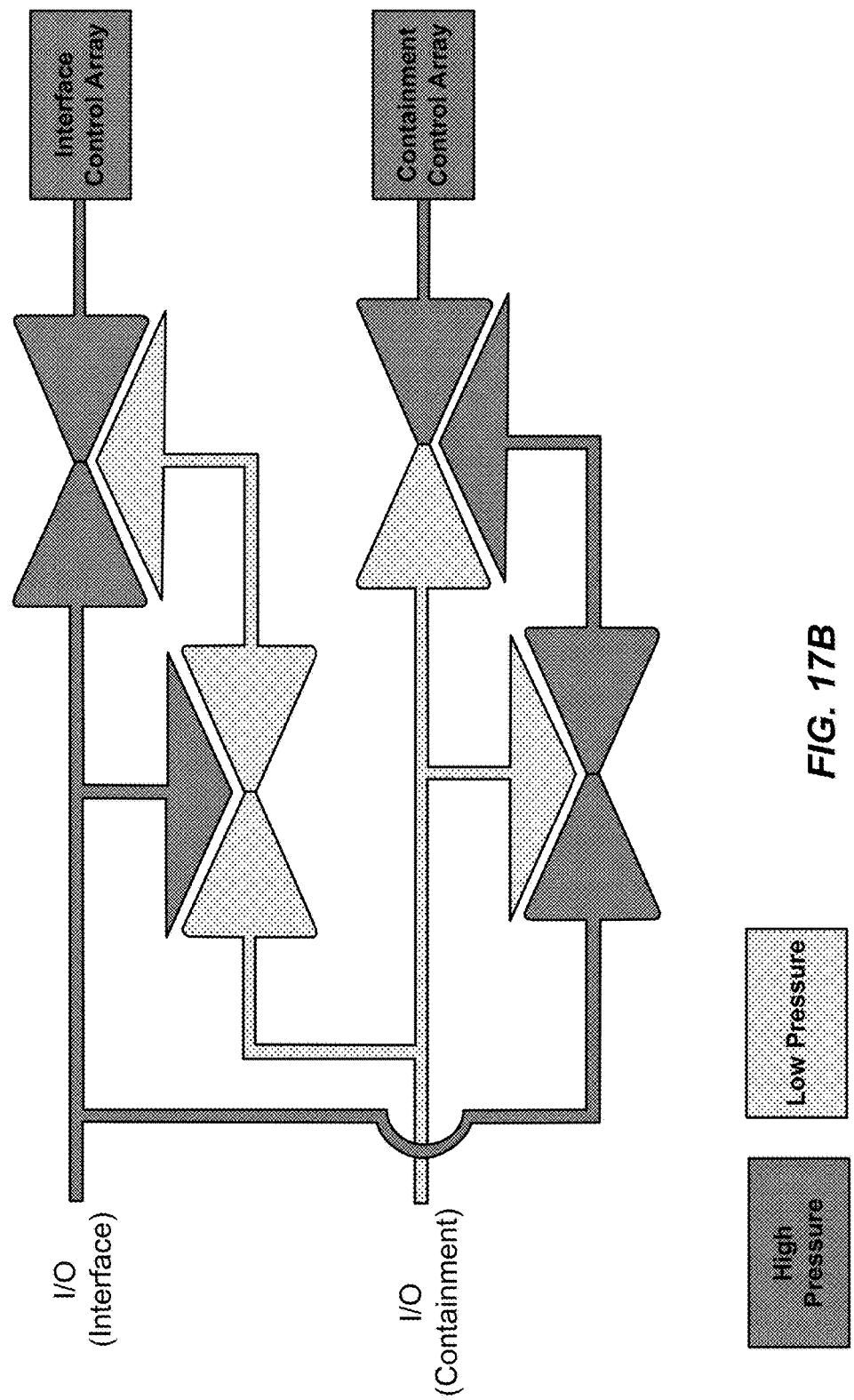
Figure 17C:
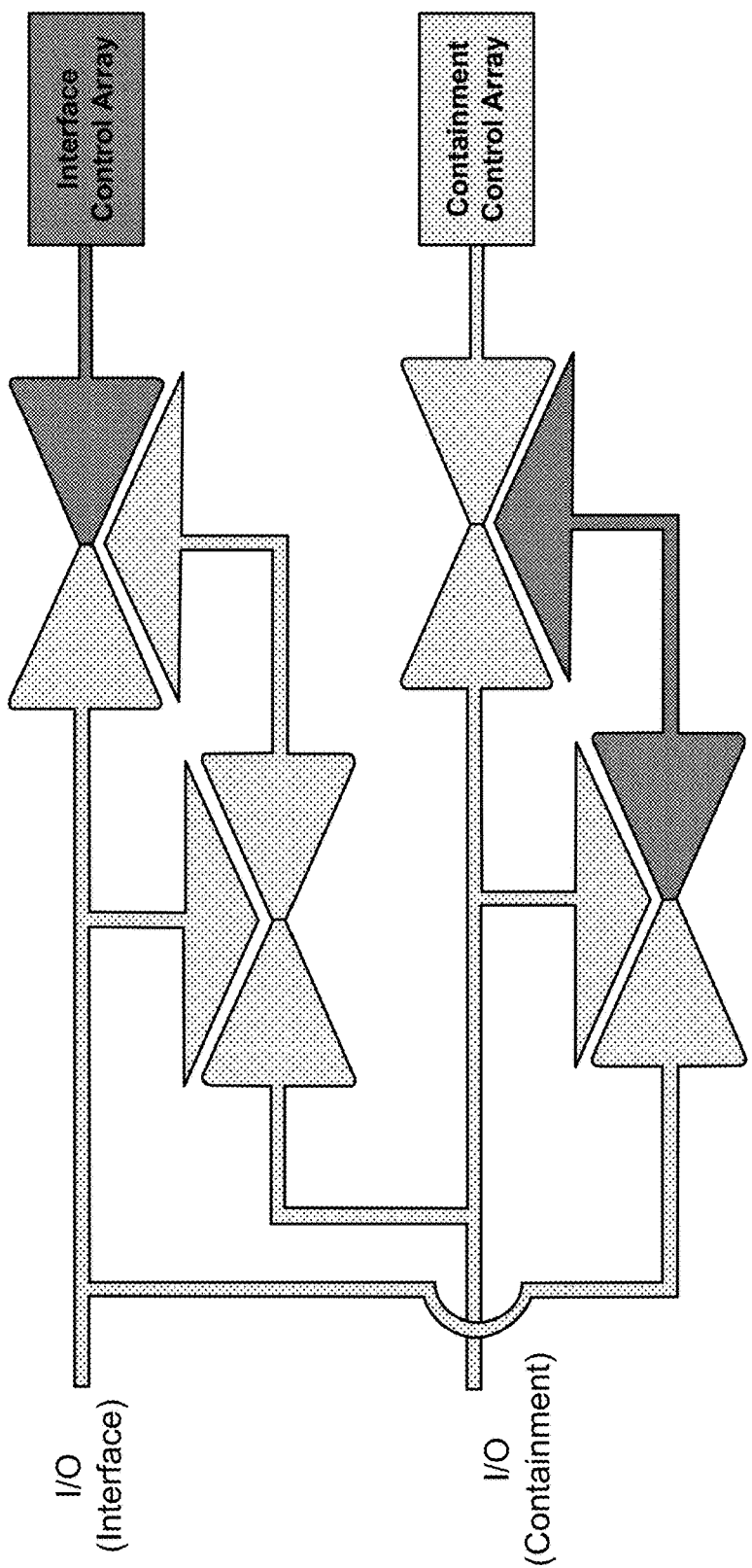

FIGS. 17A-17C are simplified schematic diagrams illustrating priming of a microfluidic array according to an embodiment of the present invention. As illustrated in these figures, sets of releasable check valves are utilized in a layered structure to provide control functionality. I/O control port 1710 and I/O control port 1720 are used to pressurize one or more control lines in communication with the releasable check valves as described below. Although I/O control port 1710 is labeled I/O (Interface) and I/O control port 1720 is labeled I/O (Containment) in conjunction with the Interface Control Array and the Containment Control Array, as we be evident in the following description, both I/O control ports are utilized in conjunction with each other to provide the functionality described herein. As shown in the inset in FIG. 17A, each releasable check valve has an input and output for fluid flow through the valve as well as a control port (Release) that is used to open the normally closed valve. In an embodiment, the control port is in fluid communication with the release pads discussed in relation to FIGS. 13A and 13B.

The releasable check valves illustrated in FIG. 17A include a first valve 1712 with an output coupled to the interface control array and a second valve 1714 with an output coupled to the release port of first valve 1712. Thus the second valve 1714 is used to control the operation (e.g., the opening and closing) of the first valve 1712. Valve 1712 provides a signal (e.g., a fluid pressure) that sets the pressure in the interface control array. The releasable check valves illustrated in FIG. 17A also include a third valve 1722 with an output coupled to the containment control array and a fourth valve 1724 with an output coupled to the release port of third valve 1722. Thus the fourth valve 1724 is used to control the operation (e.g., the opening and closing) of the third valve 1722. Valve 1722 provides a signal (e.g., a fluid pressure) that sets the pressure in the containment control array.

Although embodiments are discussed in terms of control of an interface control array and a containment control array, other microfluidic devices are included within the scope of the present invention and these are merely used by way of example. Thus, embodiments of the present invention are applicable to the control of numerous other types of microfluidic arrays.

As illustrated in FIG. 17A, a first step of a priming process is shown, with both the I/O control port 1710 and the I/O control port 1720 set at a predetermined pressure (e.g., 30 psi in the example that follows although other pressures could be utilized). The pressure in all control lines 1711, 1713, 1721, and 1723 is at 30 psi. The pressure in control line 1711 actuates the release function of valve 1714, pressurizing control line 1725, which actuates the release function of valve 1712, pressurizing control line 1717 and the interface control array. The pressure in control line 1721 actuates the release function of valve 1724, pressurizing control line 1715, which actuates the release function of valve 1722, pressurizing control line 1727 and the containment control array. Thus, all the valves are opened to pressurize both control arrays. As an example, the control lines could be primed with Krytox at 30 psi in a predetermined time period, for example about 10 minutes.

FIG. 17B illustrates the control of the control arrays during the second step in the priming process in which the pressure is withdrawn from the I/O control port 1720 while maintaining the pressure at the I/O control port 1710. The reduction in pressure of I/O control port 1720 is illustrated in FIG. 17B by the lighter shading on control lines 1721 and 1723 (representing atmospheric pressure in an embodiment). Valve 1712 remains closed when the pressure on control line 1725 is reduced, enabling application of pressure to the interface control array.

FIG. 17C illustrates reduction of pressure in I/O control port 1710 (light shading on control lines 1711 and 1713, opening valve 1722 and enabling complete pressure release from the containment control array. With the interface valves closed, sample and assays are loaded into the chip.

Figure 18A:
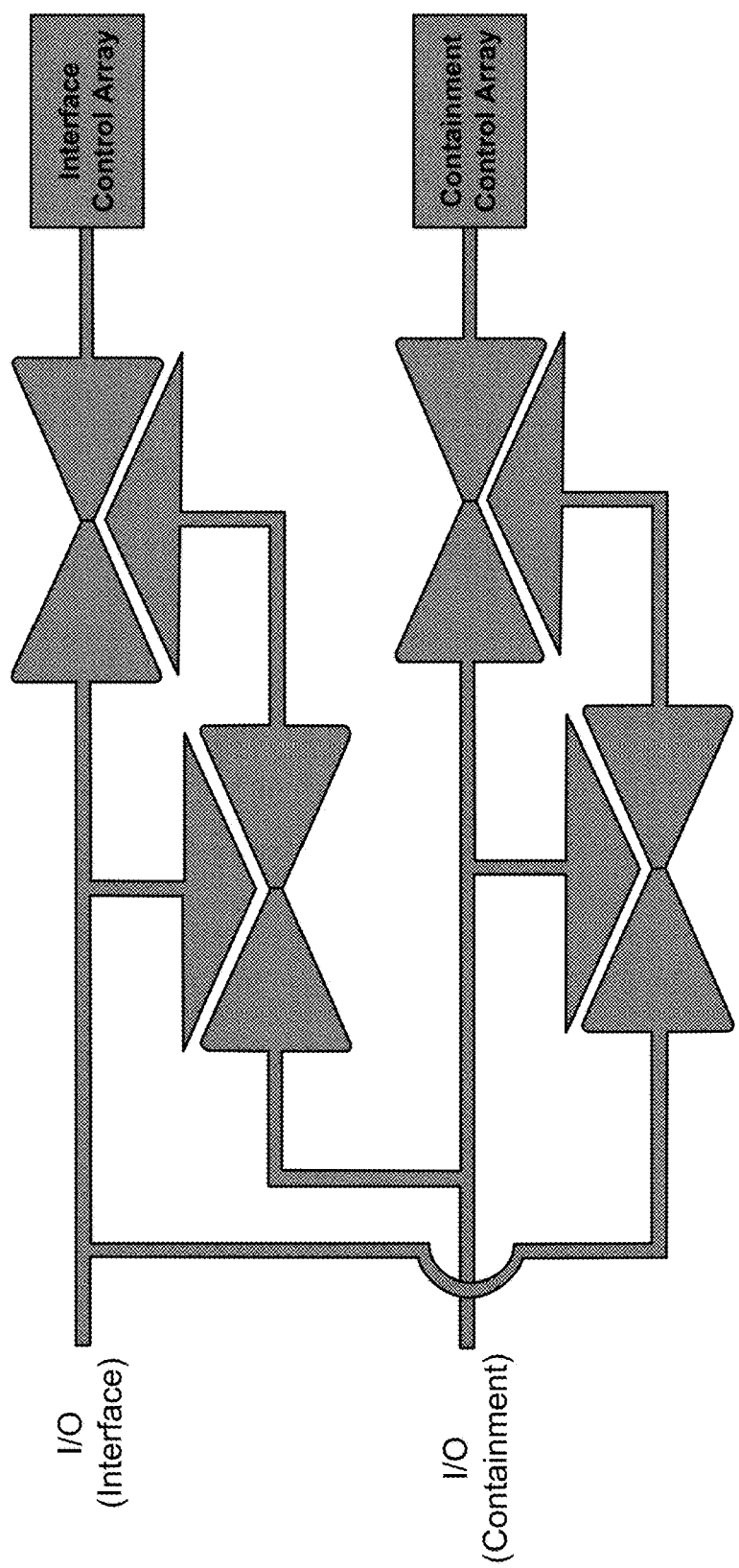
FIGS. 18A-18C are simplified schematic diagrams illustrating loading of sample and assay lines of a microfluidic array according to an embodiment of the present invention.
Figure 18B:
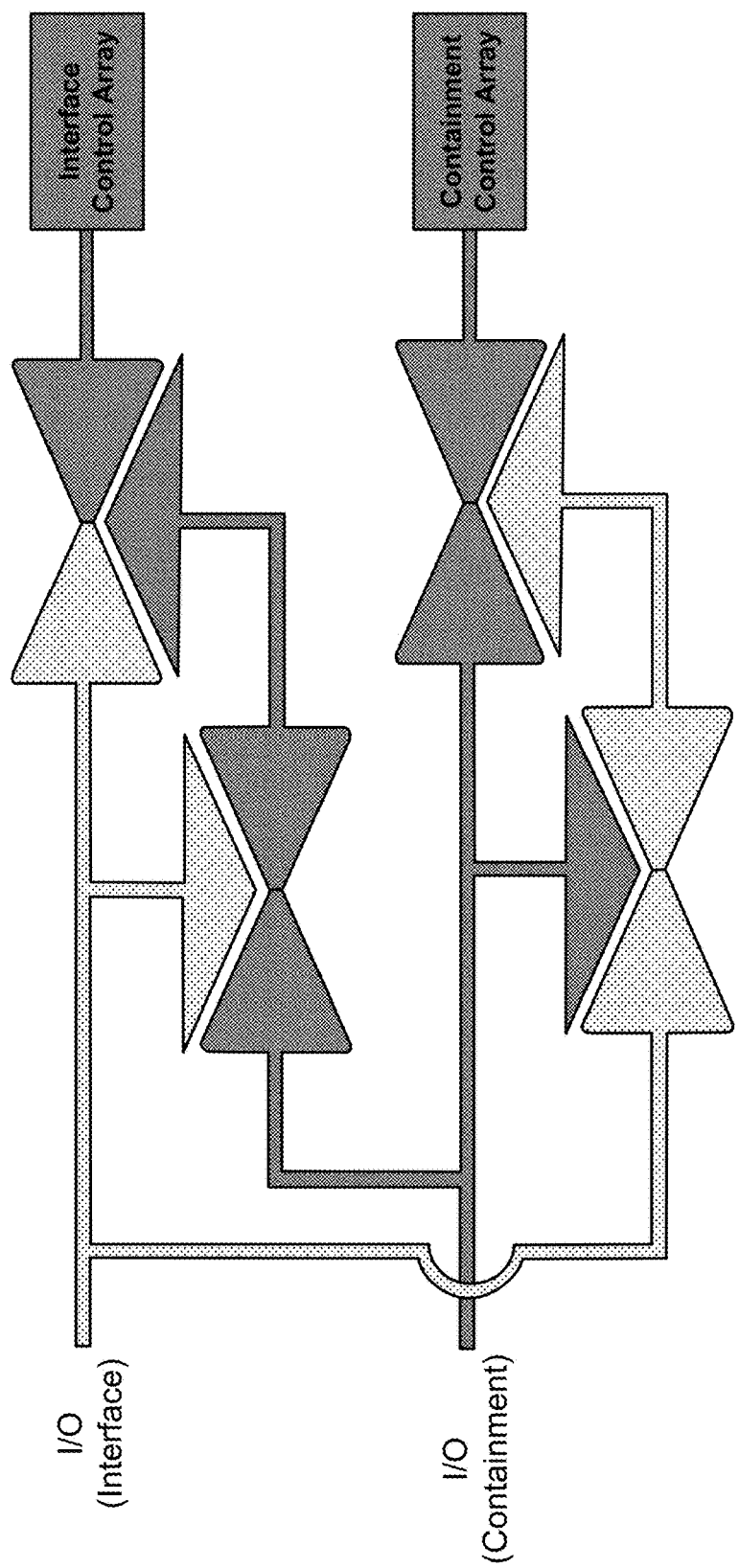
Figure 18C:
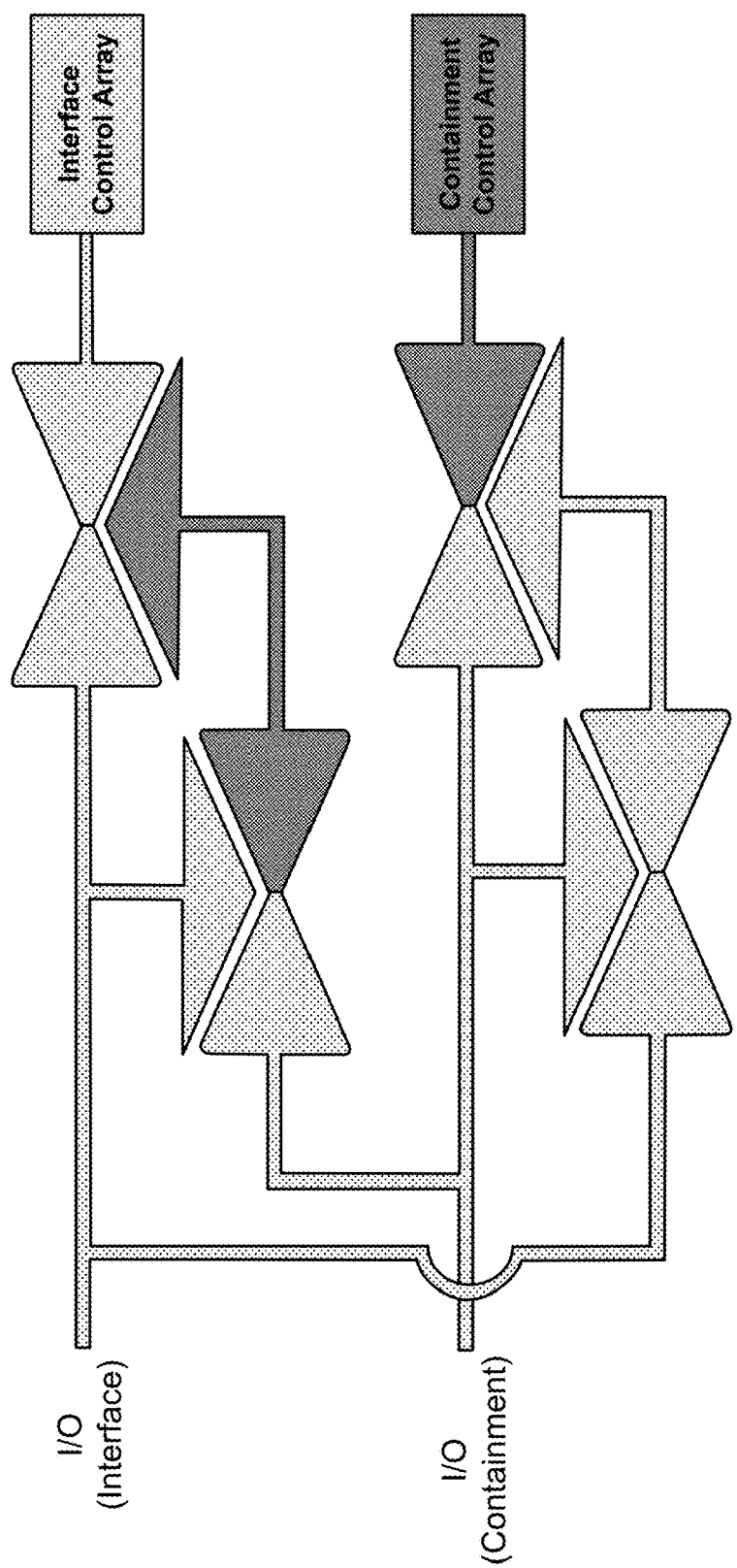

FIGS. 18A-18C are simplified schematic diagrams illustrating closing the containment valves and opening the interface valves for the sample and assays to mix according to an embodiment of the present invention. As illustrated in FIG. 18A, both the I/O control ports 1710 and 1720 are pressurized (e.g., 30 psi) to pressurize the control arrays and close all the control valves in the array.

FIG. 18B illustrates a second step of the sample and assay loading process in which the pressure on the I/O control port 1710 is reduced to atmospheric pressure while maintaining the pressure on the I/O control port 1720. This traps the pressure in the containment array and keep the interface release control valve to release the pressure from the interface array. FIG. 18C illustrates the third step of the sample and assay loading process, releasing the pressure on the I/O control port 1720 to ensure complete pressure release from the interface control array while maintaining pressurization of the containment control array. This condition enables mixing of the samples and assays as described below since, with the interface control array at atmospheric pressure, the interface valves are open, enabling mixing of the sample and assays while the containment control array is pressured with the containment valves closed.

Figure 19A:
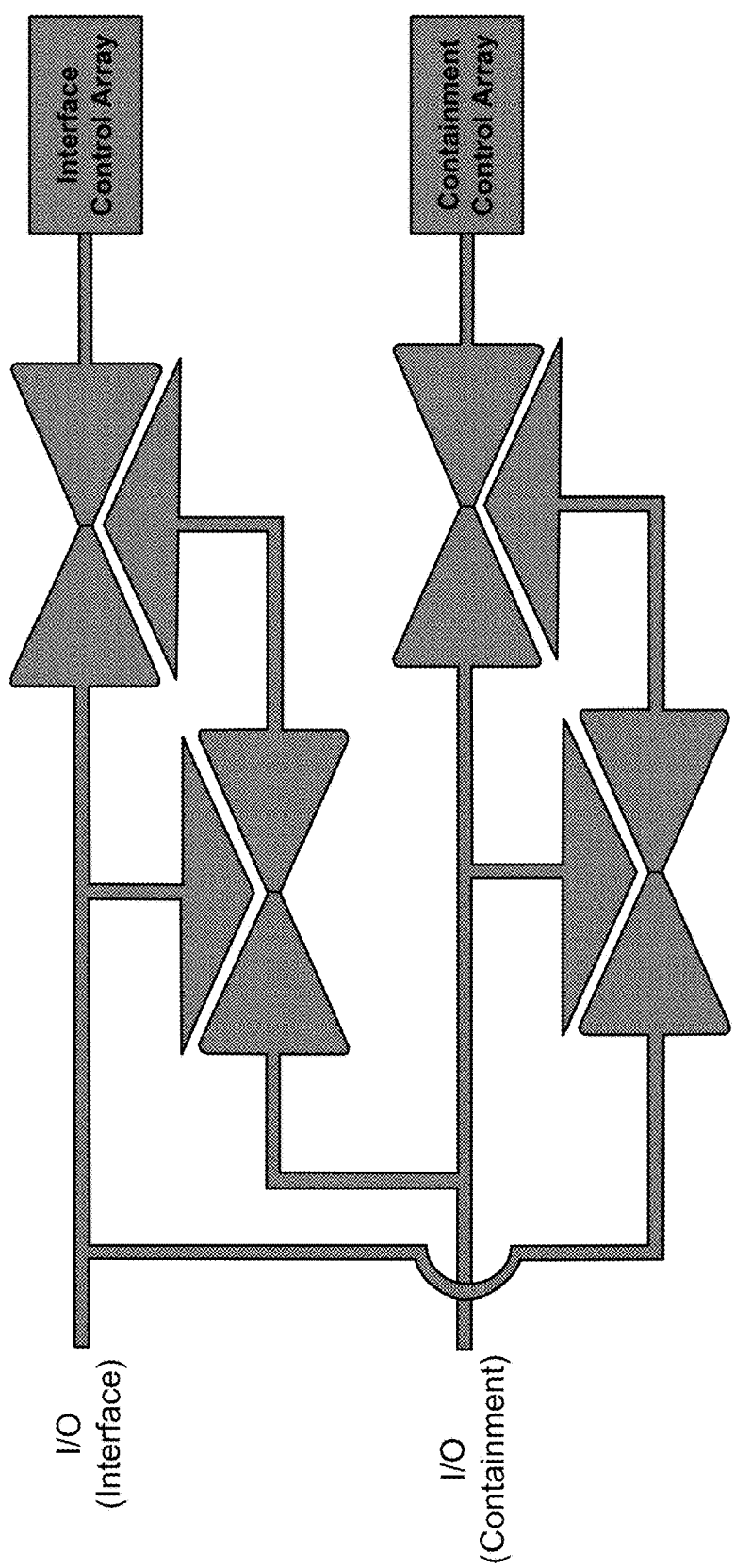
FIGS. 19A-19D are simplified schematic diagrams illustrating mixing of samples and assays in a microfluidic array according to an embodiment of the present invention.
Figure 19B:
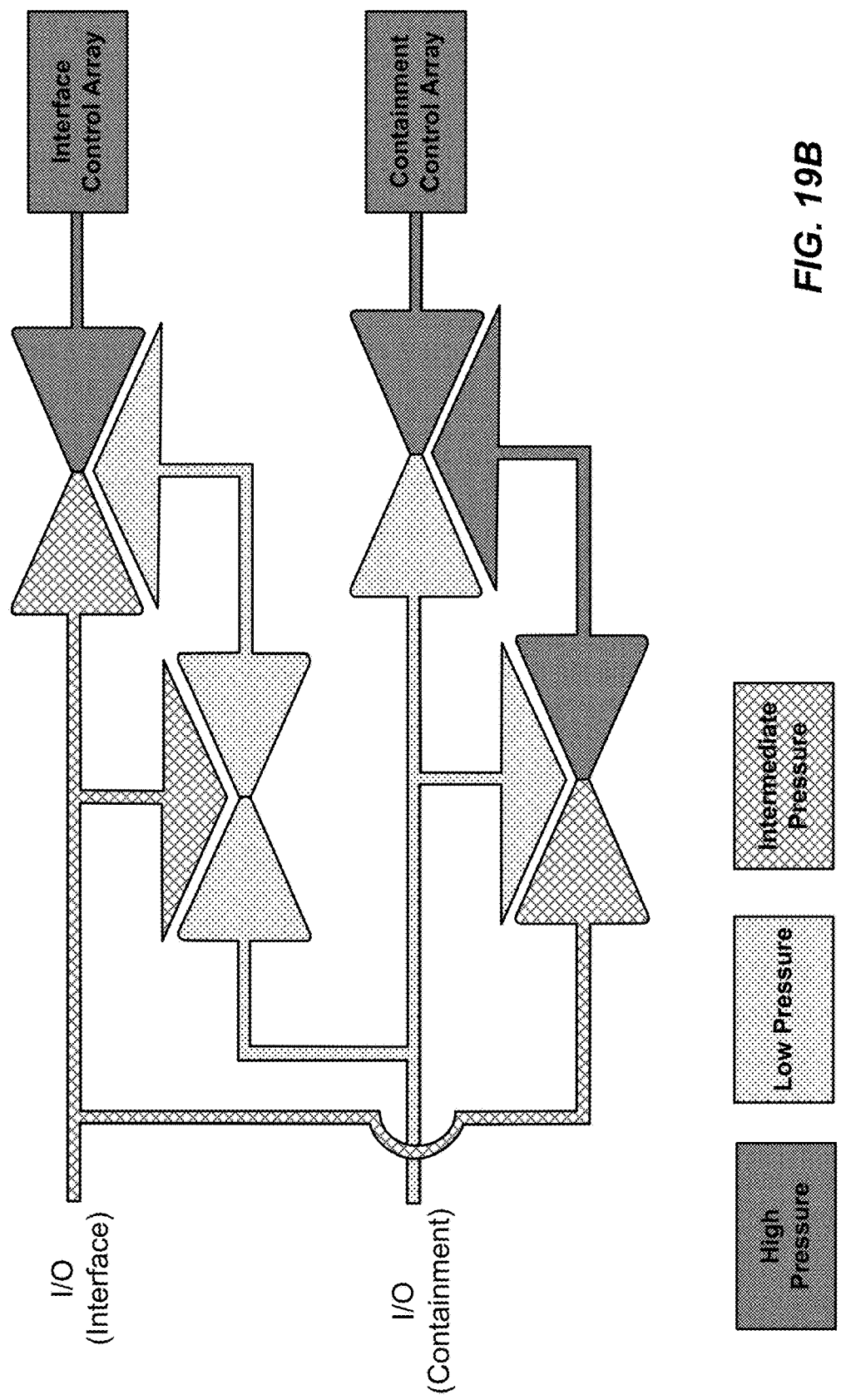

FIGS. 19A-19D are simplified schematic control diagrams illustrating closing both interface and containment valves at the same time for PCR of the sample and assay mixtures according to an embodiment of the present invention. As illustrated in FIG. 19A, both the I/O control ports 1710 and 1720 are pressurized at a predetermined pressure (e.g., 30 psi) to once again pressurize the interface and containment arrays. In FIG. 19B, the pressure on I/O control port 1710 is reduced to an intermediate pressure between a low pressure (e.g., atmospheric pressure) and the predetermined pressure and the pressure on I/O control port 1720 is reduced to the low (e.g., atmospheric pressure). In FIG. 19B, the predetermined pressure is represented by dark shading, the intermediate pressure by cross-hatched shading, and the low pressure by light shading as before. By pressurizing the I/O control port 1710 at intermediate pressure, the pressure in the valve 1714 drops to atmospheric pressure and traps pressure in the interface control array.

Figure 19C:
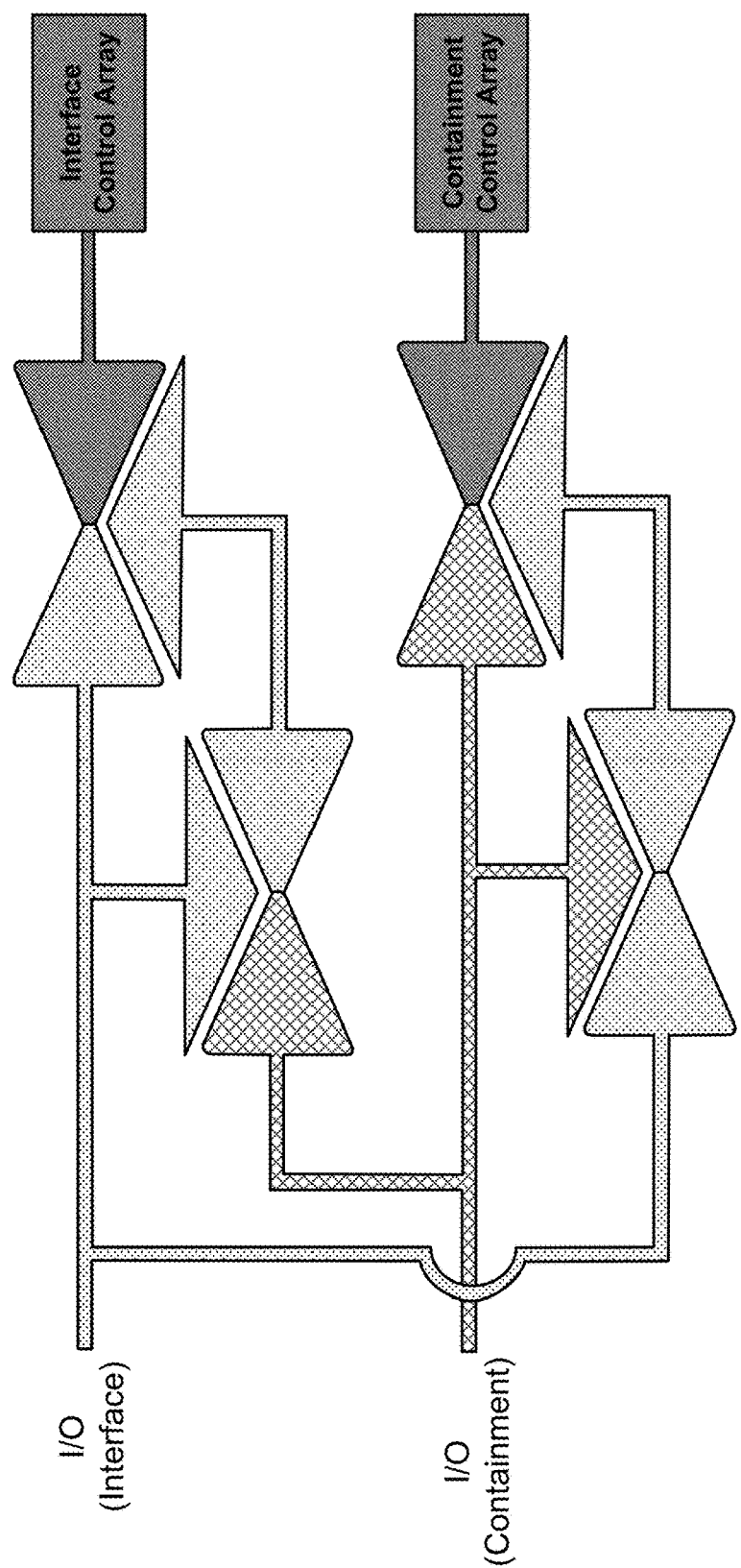

FIG. 19C illustrates a third step of the mixing process in which the pressure at I/O control port 1710 is reduced to low (e.g., atmospheric) pressure and the pressure at I/O control port 1720 is increased to the intermediate pressure. The application of intermediate pressure to control line 1721 results in the pressure in the valve 1724 dropping to atmospheric pressure and traps pressure in the containment control array.

Figure 19D:
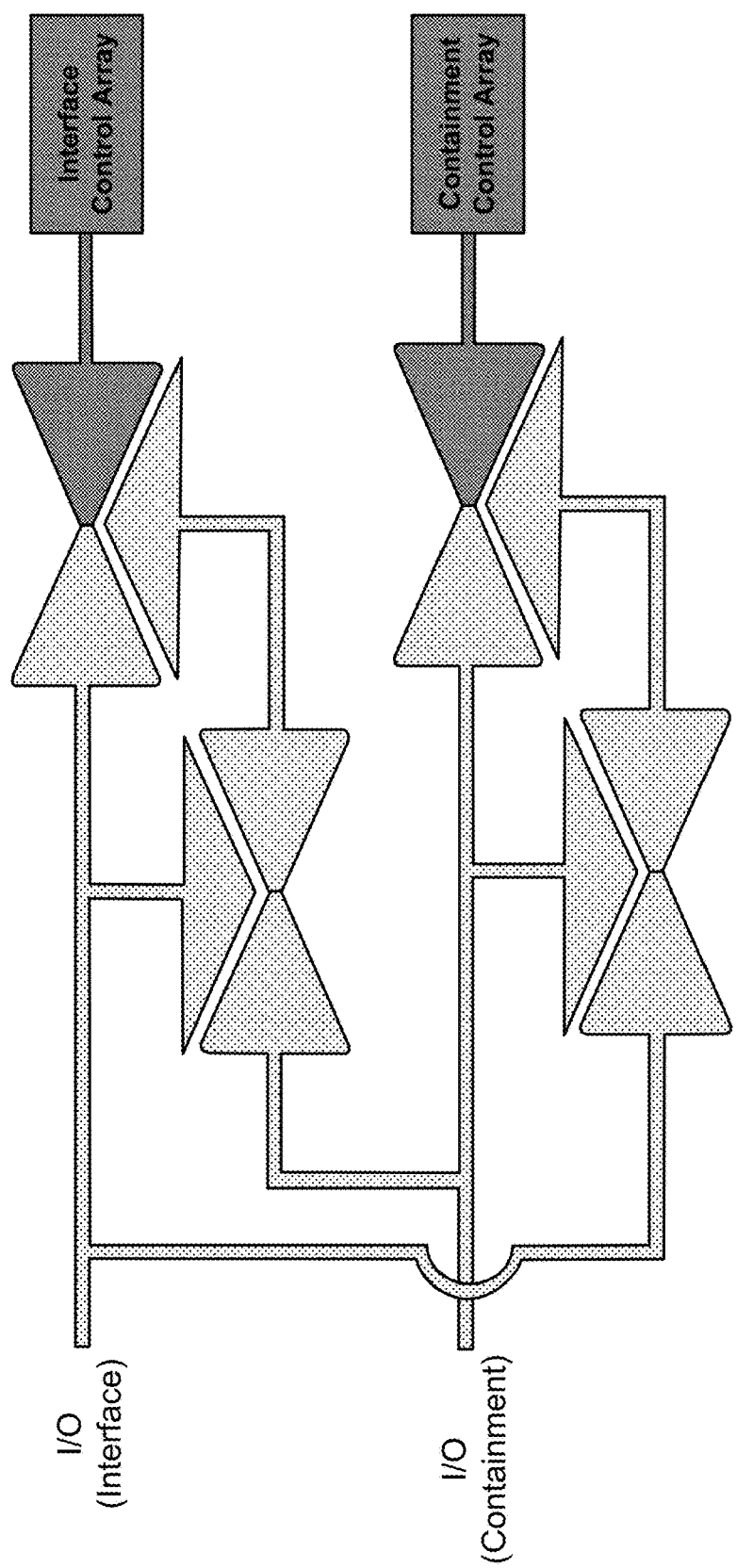

FIG. 19D illustrates removal of pressure on both I/O control ports 1710 and 1720 while both containment and interface control arrays are fully pressurized during PCR.

Table 1 provides an example pressures used in a process to prime, load, mix, and perform PCR using a microfluidic device. The pressures are related to the I/O control ports and valves illustrated in FIG. 17A. As illustrated in Table 1, the pressures at I/O control ports 1710 and 1720 drive the opening and closing of valves 1712, 1714, 1716, and 1718, thereby either opening or closing valves present in the interface control array and the containment control array.

TABLE 1

| | I/O Port 1710 | I/O Port 1720 | Valve 1712 | Valve 1712 | Valve 1722 | Valve 1724 |
|---|---|---|---|---|---|---|
| Prime | 30 | 30 | 30 | 30 | 30 | 30 |
| | 30 | 0 | 30 | 0 | (30 → 0) | 30 |
| | 0 | 0 | 30 | 0 | 0 | 30 |

TABLE 1-continued

| | I/O Port 1710 | I/O Port 1720 | Valve 1712 | Valve 1712 | Valve 1722 | Valve 1724 |
|---|---|---|---|---|---|---|
| Load | 0 | 0 | 30 | 0 | 0 | 30 |
| Mix | 30 | 30 | 30 | 30 | 30 | 30 |
| | 0 | 30 | (30 → 0) | 30 | 30 | 0 |
| | 0 | 0 | 0 | 30 | 30 | 0 |
| PCR | 30 | 30 | 30 | 30 | 30 | 30 |
| | 20 | 0 | 30 | 0 | 30 | 30 |
| | 0 | 20 | 30 | 0 | 30 | 0 |

Although pressures of 0, 20, and 30 psi are illustrated in Table 1, embodiments of the present invention are not limited to these particular pressures and other low, intermediate, and high pressures can be utilized as appropriate to the particular applications. One of ordinary skill in the art would recognize many variations, modifications, and alternatives.

Figure 20C:
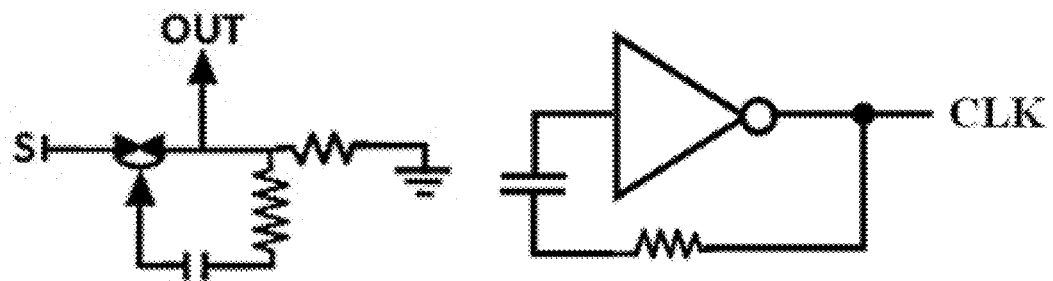
Figure 20C:
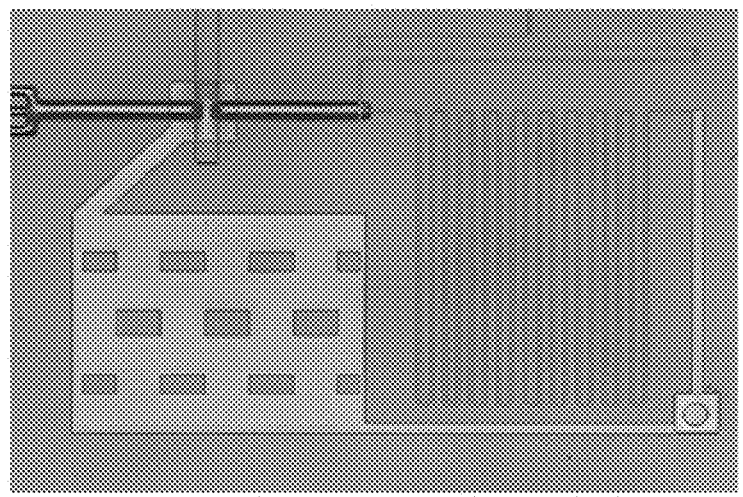

FIGS. 20A-20C are simplified schematic diagrams illustrating an oscillator according to an embodiment of the present invention. A fluidic oscillator can be fabricated from a NOT gate connected in a feedback loop where its output is fed back into its input through a fluidic resistor and capacitor in series. When the pressure signal is turned "ON" the signal travels through the loop and starts generating repetitive pressure pulses at a fixed frequency. The frequency and the amplitude of the oscillator increases proportionally with the source pressure.

Figure 21A:
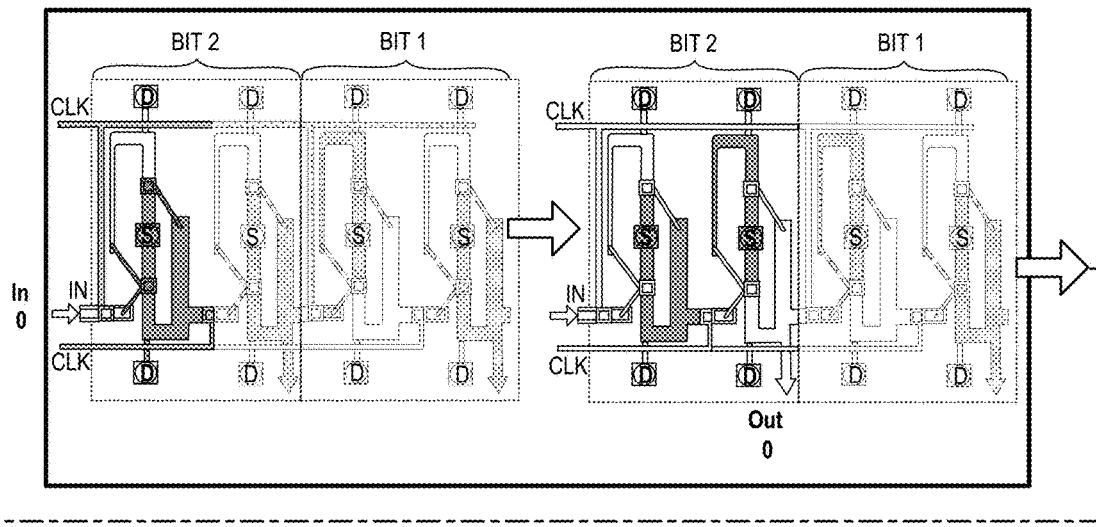
FIG. 21A shows simplified schematic diagrams illustrating states of a shift register in different clock cycles according to an embodiment of the present invention.
Figure 21A:
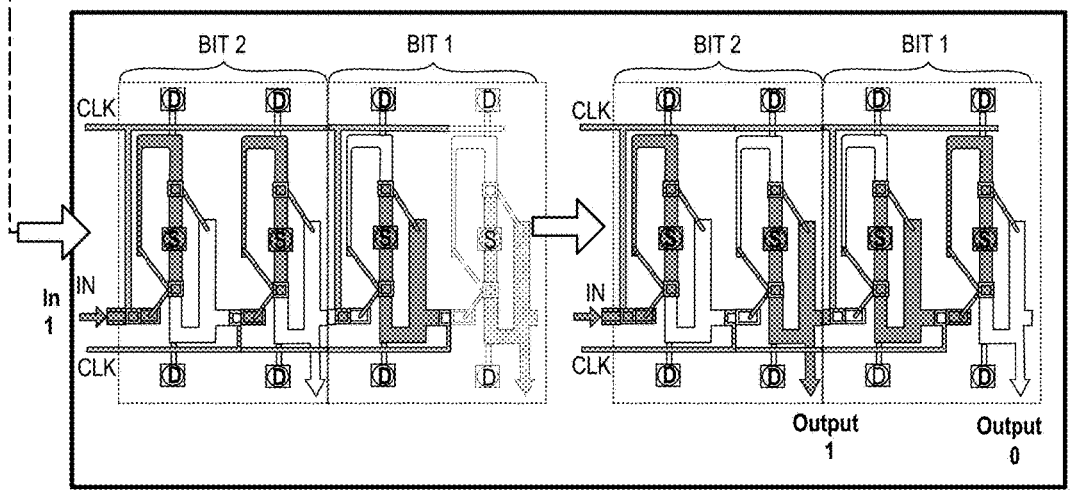

FIG. 21A shows simplified schematic diagrams illustrating states of a shift register in different clock cycles according to an embodiment of the present invention. A shift register capable of processing n+1 bits of information is formed when n D flip flops are connected sequentially.

Figure 21B:
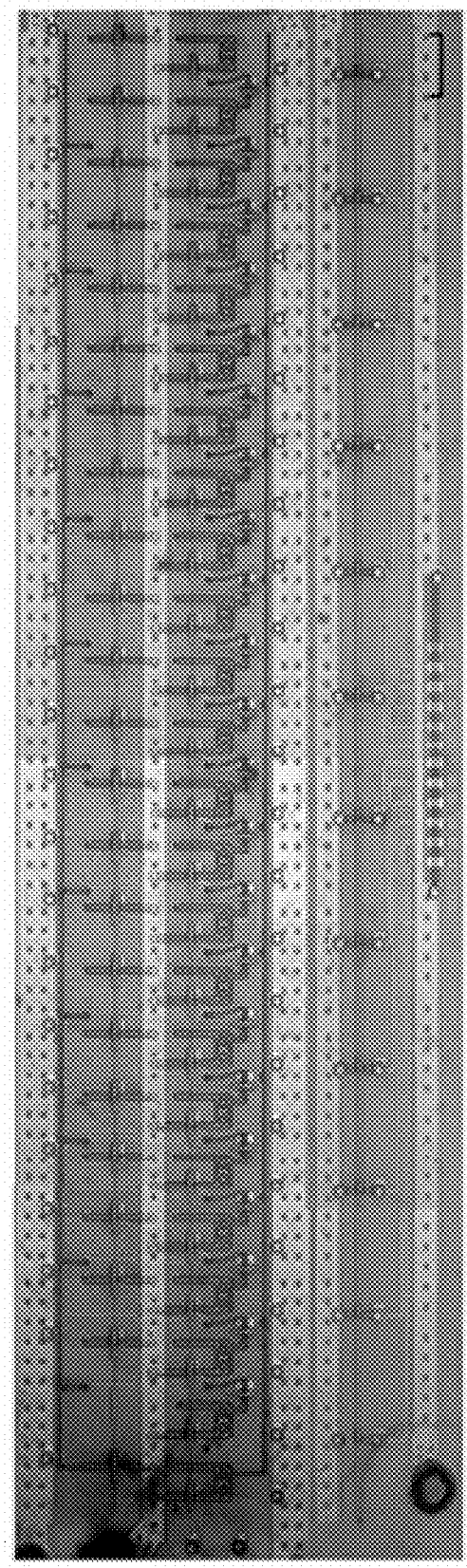
FIG. 21B is a simplified schematic diagram illustrating a shift register according to an embodiment of the present invention.

FIG. 21B is a simplified schematic diagram illustrating a shift register according to an embodiment of the present invention.

Figure 21C:
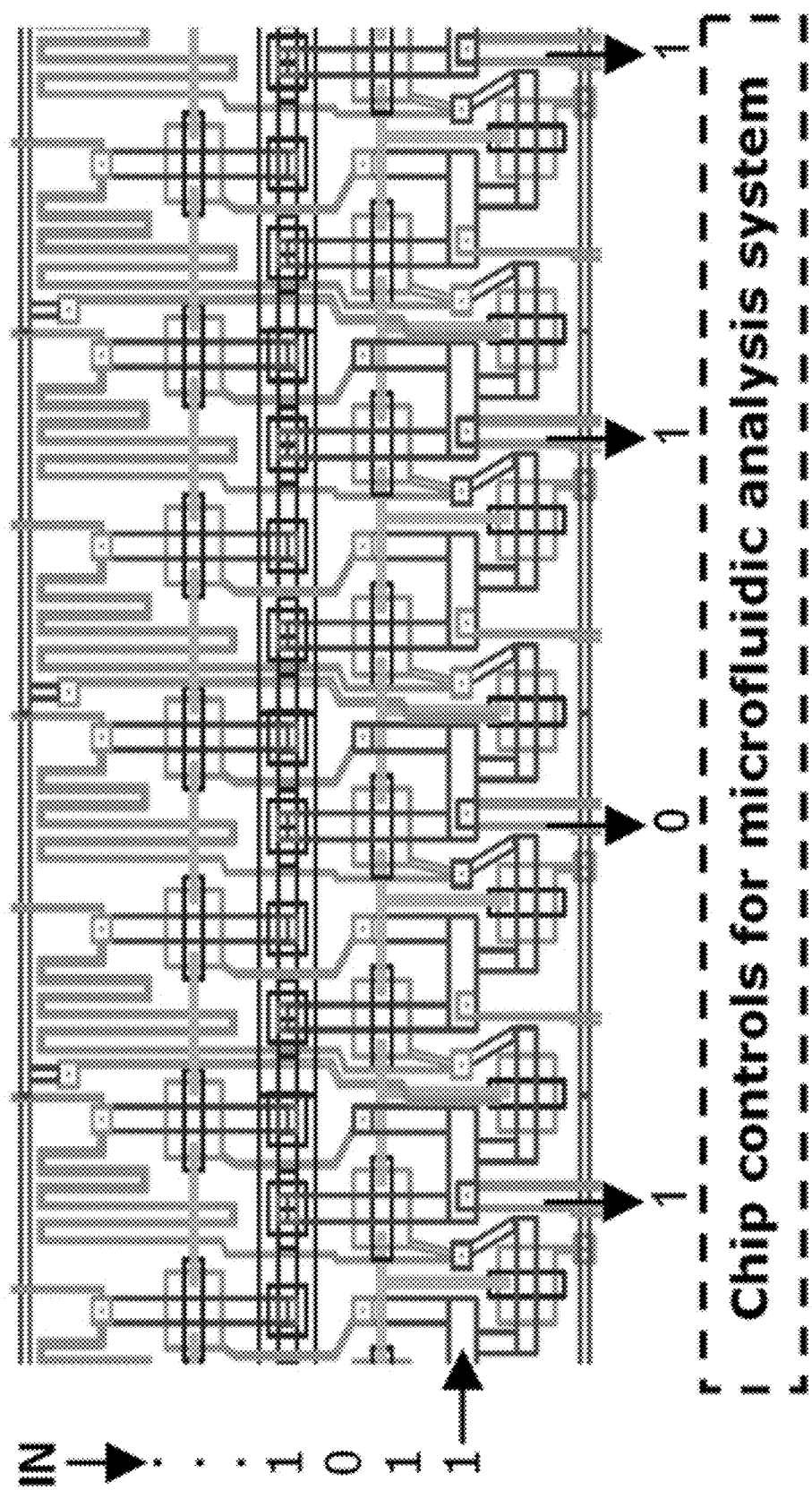
FIG. 21C is a simplified schematic diagram illustrating operation of a shift register according to an embodiment of the present invention.

FIG. 21C is a simplified schematic diagram illustrating operation of a shift register according to an embodiment of the present invention. A serial to parallel converter can be formed by combining a shift register & a trigger and has 3 active inputs—(1) Clock, (2) Input (Data), and (3) Trigger. The input line receives the data serially and processes the command sequence into parallel individually addressable command bits. Data advances by one bit through the shift register with each clock cycle. Data transfer through a 2 bit SR with each clock cycle is shown in the figures. As an example, a 12 bit shift register can be operated at speeds as high as 10 Hz according to some embodiments.

Figure 22:
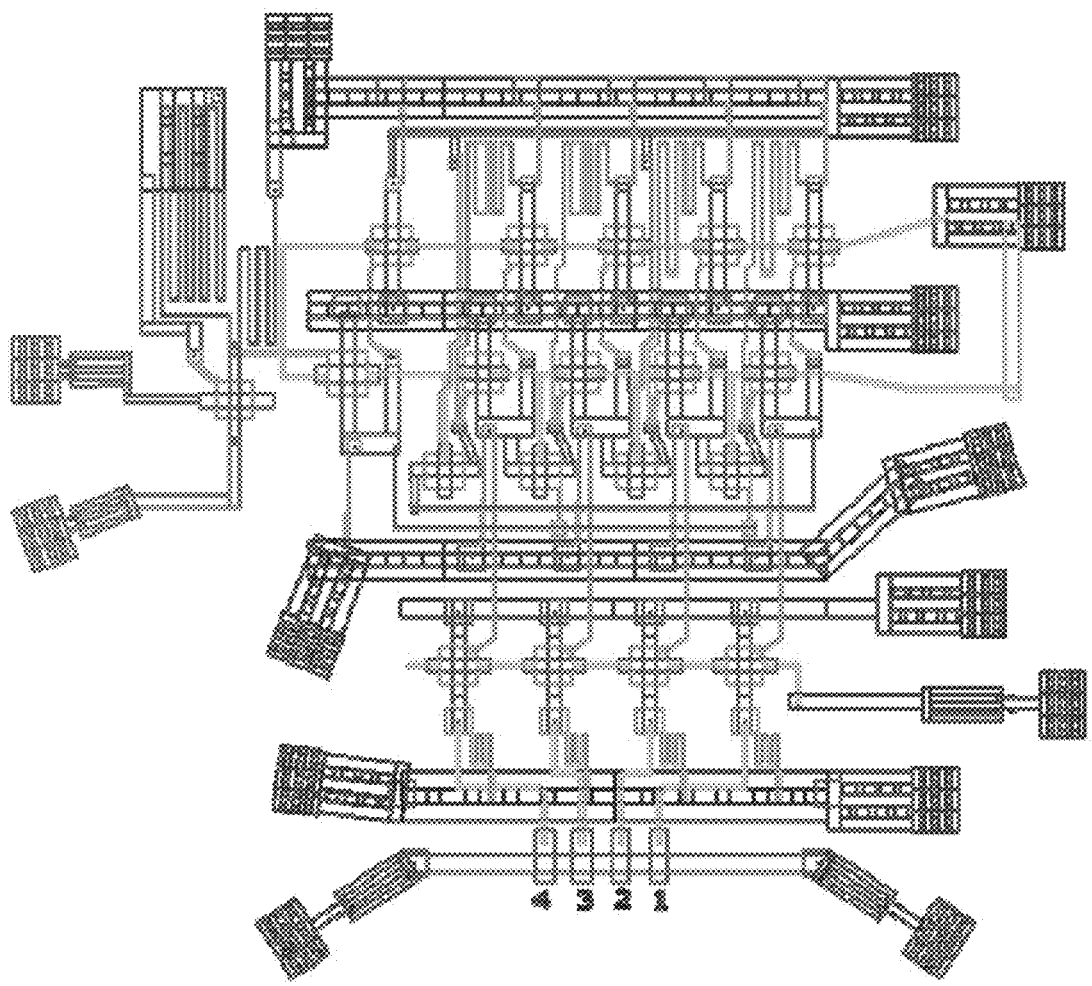
FIG. 22 is a simplified schematic diagram illustrating a pump according to an embodiment of the present invention.

FIG. 22 is a simplified schematic diagram illustrating a pump according to an embodiment of the present invention. A pump, also referred to as an autonomous pump can be fabricated according to embodiments of the present invention. As an example, a self fed single input peristaltic pump can be formed by joining two delay flip flops and continuously circulating an output similar to 1100 through the latches (individual gated flip flops) by feeding the output of the fourth latch into the first one. Output is drawn from all the latches to drive the pump. A fluidic oscillator output signal controls the clock (flip flop) which generates clock and anti clock signals. The integrated oscillator can run the pump with no active inputs.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A microfluidic system comprising:
   a substrate;
   a set of input ports coupled to the substrate;
   a set of output ports coupled to the substrate;
   a microfluidic processing system coupled to the substrate and including a plurality of processing sites, wherein the microfluidic processing system is coupled to the set of input ports and the set of output ports; and
   one or more microfluidic logic devices coupled to the substrate and operable to control at least a portion of the microfluidic processing system, wherein the one or more microfluidic logic devices comprise multiple elastomeric layers and one or more clocked flip flops, and wherein each of the one or more clocked flip flops comprise two NOT gates.

2. The microfluidic system of claim 1 wherein the plurality of processing sites are disposed in an array configuration.

3. The microfluidic system of claim 1 wherein the microfluidic processing system comprises a plurality of arrays of processing sites.

4. The microfluidic system of claim 1 wherein the one or more microfluidic logic devices comprise binary logic gates.

5. The microfluidic system of claim 4 wherein the binary logic gates comprise at least one of buffer, NOT, NOR, or NAND gates.

6. The microfluidic system of claim 1 wherein the plurality of processing sites comprise reaction chambers.

7. The microfluidic system of claim 1 further comprising a processor and memory.

8. The microfluidic system of claim 1 wherein an output of a first NOT gate of the two NOT gates serves as an input of a second NOT gate of the two NOT gates.

* * * * *